US012742008B2

(12) United States Patent
Zhou et al.

(10) Patent No.: US 12,742,008 B2
(45) Date of Patent: Sep. 22, 2026

(54) CLDN18.2/CD3 BISPECIFIC ANTIBODIES FOR THE THERAPY OF CLDN18.2-EXPRESSING SOLID TUMORS

(71) Applicant: Shandong Boan Biotechnology Co., Ltd., Yantai (CN)

(72) Inventors: Li Zhou, Yantai (CN); Avanish Varshney, Yantai (CN); Deyong Song, Yantai (CN); Chuangchuang Dong, Yantai (CN); Ninghai Wang, Yantai (CN)

(73) Assignee: Shandong Boan Biotechnology Co., Ltd., Yantai (CN)

( * ) Notice: Subject to any disclaimer, the term of this patent is extended or adjusted under 35 U.S.C. 154(b) by 524 days.

(21) Appl. No.: 18/276,159

(22) PCT Filed: Feb. 7, 2022

(86) PCT No.: PCT/CN2022/075326

§ 371 (c)(1),
(2) Date: Aug. 7, 2023

(87) PCT Pub. No.: WO2022/166940

PCT Pub. Date: Aug. 11, 2022

(65) Prior Publication Data

US 2024/0117035 A1 Apr. 11, 2024

Related U.S. Application Data

(60) Provisional application No. 63/147,233, filed on Feb. 8, 2021.

(51) Int. Cl.
*C07K 16/28* (2006.01)

(52) U.S. Cl.
CPC .......... *C07K 16/28* (2013.01); *C07K 16/2809* (2013.01); *C07K 2317/24* (2013.01); *C07K 2317/31* (2013.01); *C07K 2317/622* (2013.01); *C07K 2317/71* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,571,894 | A | 11/1996 | Wels et al. |
| 5,587,458 | A | 12/1996 | King et al. |
| 5,869,046 | A | 2/1999 | Presta et al. |
| 6,248,516 | B1 | 6/2001 | Winter et al. |
| 12,492,252 | B2 | 12/2025 | Varshney et al. |
| 12,545,730 | B2 | 2/2026 | Varshney et al. |
| 2011/0287533 | A1 | 11/2011 | Chang |
| 2012/0034228 | A1 | 2/2012 | Kufer et al. |
| 2016/0130347 | A1 | 5/2016 | Bruenker et al. |
| 2016/0215261 | A1 | 7/2016 | Li et al. |
| 2016/0264671 | A1 | 9/2016 | Kufer et al. |
| 2018/0134789 | A1 | 5/2018 | Baeuerle et al. |
| 2018/0244805 | A1 | 8/2018 | Nezu et al. |
| 2019/0284279 | A1 | 9/2019 | Kong et al. |
| 2020/0055932 | A1 | 2/2020 | Dahlhoff et al. |
| 2023/0075633 | A1 | 3/2023 | Varshney et al. |
| 2023/0357385 | A1 | 11/2023 | Varshney et al. |

FOREIGN PATENT DOCUMENTS

| | | |
|---|---|---|
| CN | 101687915 | 3/2010 |
| CN | 103833852 | 6/2014 |
| CN | 104140974 | 11/2014 |
| CN | 105829347 | 8/2016 |
| CN | 105949324 | 9/2016 |
| CN | 107043425 | 8/2017 |
| CN | 107556387 | 1/2018 |
| CN | 107614522 | 1/2018 |
| CN | 110003332 | 7/2019 |
| CN | 111196856 | 5/2020 |
| EP | 404097 | 12/1990 |
| JP | 2015536908 | 12/2015 |
| JP | 2019513014 | 5/2019 |

(Continued)

OTHER PUBLICATIONS

Xu et al. Dark horse target Claudin18.2 opens new battlefield for pancreatic cancer. Front. Oncol., Mar. 5, 2024, pp. 1-11. (Year: 2024).*
Almagro et al., "Humanization of antibodies," Frontiers in Bioscience, Jan. 2008, 13:1619-1633.
Casset et al., "A peptide mimetic of an anti-CD4 monoclonal antibody by rational design," Biochemical and Biophysical Research Communications, Jul. 2003, 307(1):198-205.
Chen et al., "Selection and Analysis of an Optimized Anti-VEGF Antibody: Crystal Structure of an Affinity-matured Fab in Complex with Antigen," J. Mol. Biol., Nov. 1999, 293(4):865-881.
Lamminmaki et al., "Crystal Structure of a Recombinant Anti-estradiol Fab Fragment in Complex with 17 Beta-Estradiol*,"The Journal of Biological Chemistry, Sep. 2001, 276(39):36687-36694.
MacCallum et al., "Antibody-antigen Interactions: Contact Analysis and Binding Site Topography," J. Mol. Biol., Oct. 1996, 262(5):732-745.

(Continued)

*Primary Examiner* — Maher M Haddad
(74) *Attorney, Agent, or Firm* — Fish & Richardson P.C.

(57) ABSTRACT

The present application provides CLDN18.2 antibodies or antigen binding fragments thereof and related CLDN18.2/CD3 bispecific antibodies, as well as corresponding nucleic acids encoding same, vectors comprising such nucleic acids, host cells transfected with such nucleic acids or vectors. The present application further relates to isolated CLDN18.2 antibodies or antigen binding fragments thereof and related CLDN18.2/CD3 bispecific antibodies, pharmaceutical compositions comprising such antibodies, antigen binding fragments, bispecific antibodies, nucleic acids, vectors, or host cells and optionally a pharmaceutically acceptable carrier, and methods of treating cancer in a subject in need thereof by administering such pharmaceutical compositions. The cancers treated in accordance with the present application include CLDN18.2-positive cancers, such as, inter alia, gastric cancer and pancreatic cancer.

19 Claims, 13 Drawing Sheets

Specification includes a Sequence Listing.

(56) References Cited

FOREIGN PATENT DOCUMENTS

| | | |
|---|---|---|
| WO | WO 1993001161 | 1/1993 |
| WO | WO 1993016185 | 8/1993 |
| WO | WO 2010037835 | 4/2010 |
| WO | WO 2010088522 | 8/2010 |
| WO | WO 2013070468 | 5/2013 |
| WO | WO 2013167153 | 11/2013 |
| WO | WO 2014056783 | 4/2014 |
| WO | WO 2017118675 | 7/2017 |
| WO | WO 2017156178 | 9/2017 |
| WO | WO 2017159287 | 9/2017 |
| WO | WO 2018114754 | 6/2018 |
| WO | WO 2019086497 | 5/2019 |
| WO | WO 2019241216 | 12/2019 |
| WO | WO 2020025792 | 2/2020 |
| WO | WO 2020135674 | 7/2020 |
| WO | WO 2020139956 | 7/2020 |
| WO | WO 2020147321 | 7/2020 |
| WO | WO 2021121215 | 6/2021 |
| WO | WO 2022166940 | 8/2022 |

OTHER PUBLICATIONS

Padlan et al., "Structure of an antibody-antigen complex: Crystal structure of the HyHEL-10 Fab-lysozyme complex," Proc. Natl. Acad. Sci., Aug. 1989, 86(15):5938-5942.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, Sep. 2002, 169(6):3076-3084.
Rudikoff et al., "Single amino acid substitution altering antigen-binding specificity," Proc. Natl. Acad. Sci., Mar. 1982, 79(6):1979-1983.
Vajdos et al., "Comprehensive Functional Maps of the Antigenbinding Site of an Anti-ErbB2 Antibody Obtained with Shotgun Scanning Mutagenesis," J. Mol. Biol., Jul. 2002, 320(2):415-428.
Wu et al., "Humanization of a Murine Monoclonal Antibody by Simultaneous Optimization of Framework and CDR Residues," J. Mol. Biol., Nov. 1999, 294(1):151-162.
Extended European Search Report in European Appln No. 20902716.8, mailed on Jul. 17, 2023, 15 pages.
Almagro et al., "Humanization of antibodies," Front Biosci, Jan. 2008, 13:1619-33.
Bacac et al., "A Novel Carcinoembryonic Antigen T-Cell Bispecific Antibody (CEA TCB) for the Treatment of Solid Tumors," Clin Cancer Res, Jul. 2016, 22(13):3286-97.
Brinkmann et al., "The making of bispecific antibodies," MABS, Jan. 2017, 9(2):182-212.
Cao et al., "Improved chemotherapy for hepatocellular carcinoma," Anticancer Research, Apr. 1, 2012, 32(4):1379-1386.
Cartellieri et al., "Chimeric antigen receptor-engineered T cells for immunotherapy of cancer," Journal of Biomedicine and Biotechnology, May 5, 2010, 2010(956304): 1-14.
Chothia et al., "Canonical Structures for the Hypervariable Regions of Immunoglobulins," J Mol Biol, Aug. 1987, 196(4):901-17.
Filmus et al., "Glypican-3: a marker and a therapeutic target in hepatocellular carcinoma," The FEBS Journal, May 2013, 280(10):2471-2476.
Filmus et al., "Glypicans: proteoglycans with a surprise," The Journal of Clinical Investigation, Aug. 15, 2001, 108(4):497-501.
GenBank Accession No. AFM30911.1, "glypican 3 isoform 2 precursor [*Homo sapiens*]," Jun. 18, 2012, 2 pages.
Grupp et al., "Adoptive cellular therapy," Cancer immunology and immunotherapy, Aug. 11, 2010, 149-172.
Handbook of Experimental Pharmacology vol. 113: The Pharmacology of Monoclonal Antibodies, Rosenberg et al (ed)., 1994, Chapter 11, 47 pages.
Hayward et al., "Lysis of CD3 hybridoma targets by cloned human CD4 lymphocytes," Immunology, May 1988, 64(1):87-92.
Heeley et al., "Mutations flanking the polyglutamine repeat in the modulatory domain of rat glucocorticoid receptor lead to an increase in affinity for hormone," Endocr Res, Aug. 2002, 28(3):217-29.
Holliger et al., "'Diabodies': Small bivalent and bispecific antibody fragments," Proc Natl Acad Sci USA, Jul. 1993, 90(14):6444-48.
Huang et al., "Tailoring cytolytic activity, proliferation and cytokine release via CD3 engineering of DART molecules for redirected T-cell killing," Keystone Symposium "Antibodies as drugs: Translating molecules into treatments," Mar. 1, 2018, 1 page.
Hudson et al., "Engineered antibodies," Nature Medicine, Jan. 2003, 9(1):129-134.
Huston et al., "Protein Engineering of Single-Chain Fv Analogs and Fusion Proteins," Methods Enzymol, 1991, 203:46-88.
International Preliminary Report on Patentability in International Appln. No. PCT/CN2020/136452, mailed on Jun. 30, 2022, 7 pages.
International Preliminary Report on Patentability in International Appln. No. PCT/CN2021/103447, mailed on Jan. 12, 2023, 6 pages.
International Search Report and Written Opinion in International Appln. No. PCT/CN2020/136452, mailed on Mar. 12, 2021, 13 pages.
International Search Report and Written Opinion in International Appln. No. PCT/CN2021/103447, mailed on Oct. 9, 2021, 14 pages.
International Search Report and Written Opinion in International Appln. No. PCT/CN2022/075326, mailed on May 11, 2022, 16 pages.
Ishiguro et al., "An anti-glypican 3/CD3 bispecific T cell-redirecting antibody for treatment of solid tumors," Science Translational Medicine, Jan. 2017, 9(410):eaa14291, 14 pages.
Johnson et al., "Construction of single-chain Fv derivatives monoclonal antibodies and their production in *Escherichia coli*," Methods Enzymol, 1991, 203:88-98.
Kipriyanov et al., "Two amino acid mutations in an anti-human CD3 single chain Fv antibody fragment that affect the yield on bacterial secretion but not the affinity," Protein Eng, Apr. 1997, 10(4):445-53.
Kuby Immunology, 6th ed., Kindt et al.(ed)., 2007, Chapter 4, p. 91, 1 page.
Labrijn et al., "Bispecific antibodies: a mechanistic review of the pipeline," Nat Rev Drug Discov, Aug. 2019, 18:585-608.
Lau et al., "Loss of the imprinted IGF2/cation-independent mannose 6-phosphate receptor results in fetal overgrowth and perinatal lethality," Genes & Development, Dec. 15, 1994, 8(24):2953-2963.
Ledbetter et al., "Valency of CD3 binding and internalization of the CD3 cell-surface complex control T cell responses to second signals: distinction between effects on protein kinase C, cytoplasmic free calcium, and proliferation," J Immunol, Jun. 1986, 136(11):3945-52.
Liljeblad et al., "Analysis of agalacto-IgG in rheumatoid arthritis using surface plasmon resonance," Glycoconj J, May 2000, 17(5):323-9.
Ludwig et al., "Mouse mutants lacking the type 2 IGF receptor (IGF2R) are rescued from perinatal lethality in Igf2 and Igf1r Null backgrounds," Developmental Biology, Aug. 1, 1996, 177(2):517-535.
Mølgaard et al., "Balanced secretion of anti-CEA × anti-CD3 diabody chains using the 2A self-cleaving peptide maximizes diabody assembly and tumor-specific cytotoxicity," Gene Ther, Apr. 2017, 24(4):208-14.
Moore et al., "Tuning T cell affinity improves efficacy and safety of anti-CD38 x anti-CD3 bispecific antibodies in monkeys—a potential therapy for multiple myeloma," Blood, Dec. 3, 2015, 126(23):1798.
Office Action in Chinese Appln. No. 202110794916.9, dated Aug. 9, 2022, 5 pages (with English Translation).
Office Action in Chinese Appln. No. 202110794916.9, dated Jun. 10, 2022, 13 pages (with English Translation).
Partial Supplemental European Search Report in European Appln. No. 20902716.8, mailed on Apr. 12, 2023, 18 pages.
Savoldo et al., "CD28 costimulation improves expansion and persistence of chimeric antigen receptor-modified T cells in lymphoma patients," The Journal of Clinical Investigation, May 2, 2011, 121(5):1822-1826.
Suurs et al., "A review of bispecific antibodies and antibody constructs in oncology and clinical challenges," Pharmacology & Therapeutics, Sep. 1, 2019, 201:103-119.

(56) References Cited

OTHER PUBLICATIONS

Tabernero et al., "Phase Ia and Ib studies of the novel carcinoembryonic antigen (CEA) T-cell bispecific (CEA CD3 TCB) antibody as a single agent and in combination with atezolizumab: Preliminary efficacy and safety in patients with metastatic colorectal cancer (mCRC)," Abstract, Presented at Proceedings of 2017 ASCO Annual Meeting I, Chicago, IL, Jun. 2-6, 2017; J Clin Oncol, May 2017, 35(15)(Suppl.):3002.
Vafa et al., "Perspective: Designing T-cell engagers with better therapeutic windows," Frontiers in Oncology, Apr. 15, 2020, 10(446):1-7.
Wang et al., "Regulation of embryonic growth and lysosomal targeting by the imprinted Igf2/Mpr gene," Nature, Dec. 1, 1994, 372(6505):464-467, (Abstract Only).
Wu et al., "Construction of GPC3-CAR-T cell targeting hepatocellular carcinoma and identification of its function," Chin J. Cancer Biother., Jul. 2017, 24(7):748-755 (with English abstract).
Yang et al., "A common pathway for T lymphocyte activation involving both the CD3-Ti complex and CD2 sheep erythrocyte receptor determinants," J Immunol, Aug. 1986, 137(4):1097-100.
Yaokai, "Anti-GPC3 × CD3 bispecific antigens the construction of the body and its activities against liver cancer," May 2018, Thesis for the master's degree, Xiamen University, May 2018, 84 pages, (with English abstract).

* cited by examiner

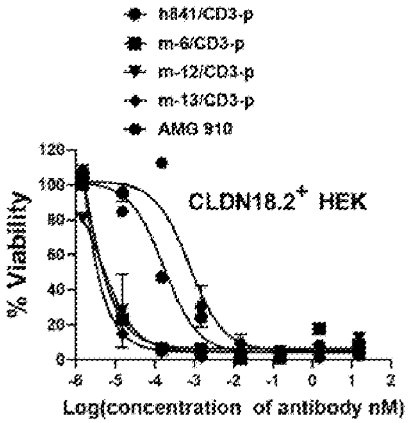
Fig. 5A
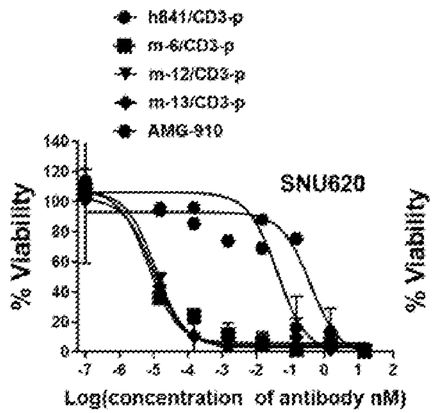
Fig. 5B
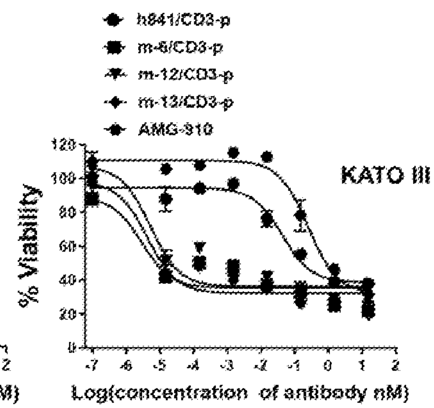
Fig. 5C
| Antibody | EC50 (nM) |
|---|---|
| h841/CD3-p | 0.00016 |
| m-6/CD3-p | 1.237e-006 |
| m-12/CD3-p | 4.295e-006 |
| m-13/CD3-p | 7.50e-008 |
| AMG-910 | 0.00076 |
Fig. 5D
| Antibody | EC50 (nM) |
|---|---|
| h841/CD3-p | 0.0417 |
| m-6/CD3-p | 7.180e-006 |
| m-12/CD3-p | 1.142e-005 |
| m-13/CD3-p | 1.017e-005 |
| AMG-910 | 0.379 |
Fig. 5E
| Antibody | EC50 (nM) |
|---|---|
| h841/CD3-p | 0.041 |
| m-6/CD3-p | 2.91e-006 |
| m-12/CD3-p | 5.27e-006 |
| m-13/CD3-p | 4.29e-006 |
| AMG-910 | 0.250 |
Fig. 5F

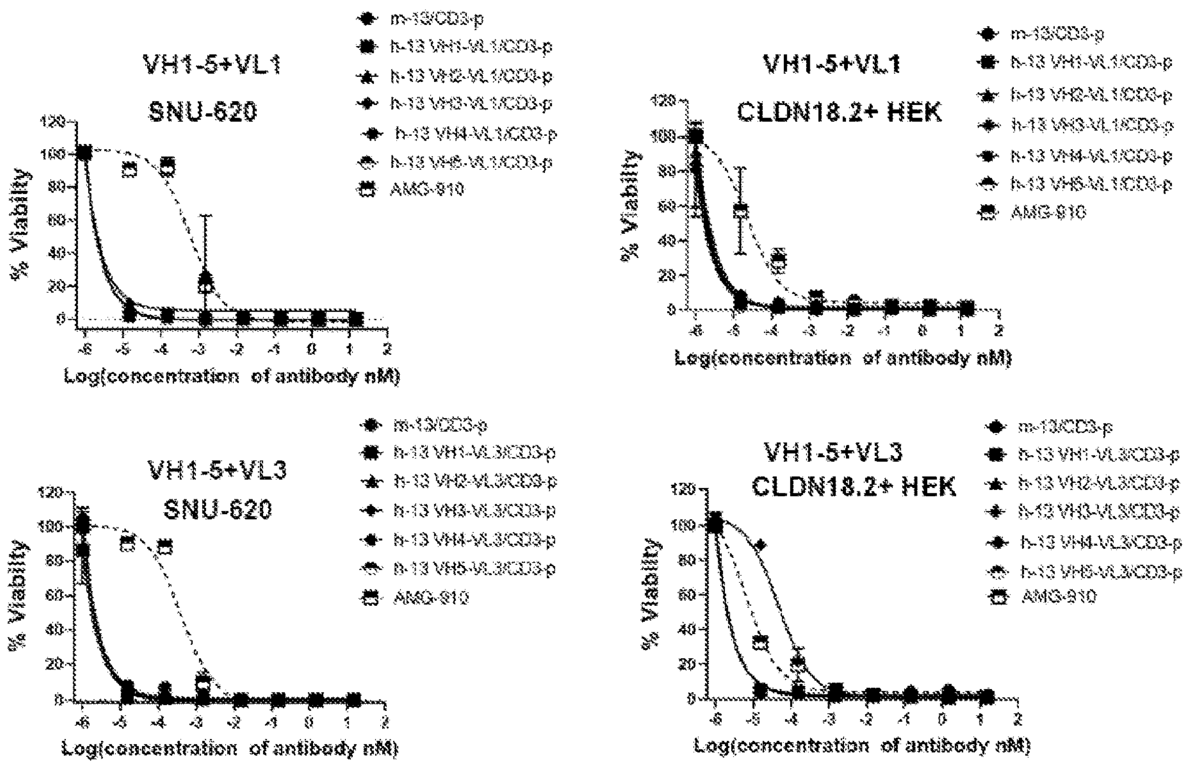
Fig.13
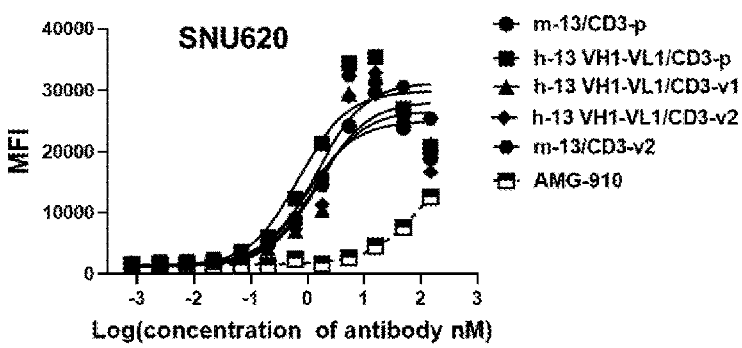
Fig.14A
| Antibody | EC50(nM) | Span |
|---|---|---|
| m-13/CD3-p | 0.982 | 23577 |
| h-13 VH1-VL1/CD3-p | 0.696 | 28702 |
| h-13 VH1-VL1/CD3-v1 | 1.568 | 26970 |
| h-13 VH1-VL1/CD3-v2 | 1.307 | 25396 |
| m-13/CD3-v2 | 1.416 | 29914 |
| AMG-910 | 87.76 | 17279 |
Fig.14 B

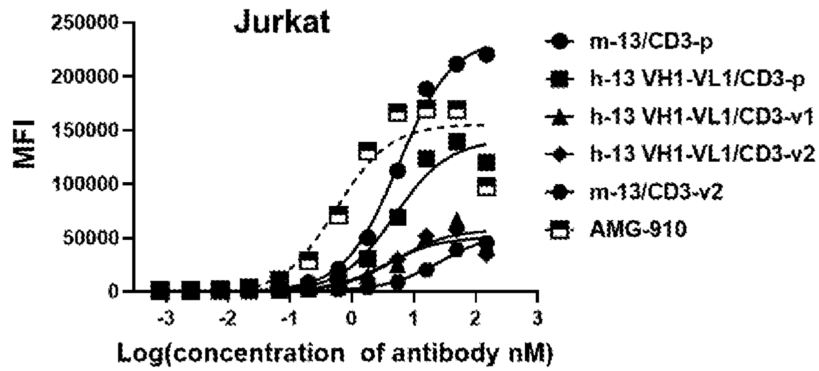
Fig.14C
| Antibody | EC50(nM) | Span |
|---|---|---|
| m-13/CD3-p | 5.629 | 235242 |
| h-13 VH1-VL1/CD3-p | 4.871 | 141711 |
| h-13 VH1-VL1/CD3-v1 | 4.866 | 57515 |
| h-13 VH1-VL1/CD3-v2 | 3.534 | 50753 |
| m-13/CD3-v2 | 26.49 | 53959 |
| AMG-910 | 0.5498 | 158587 |
Fig.14D
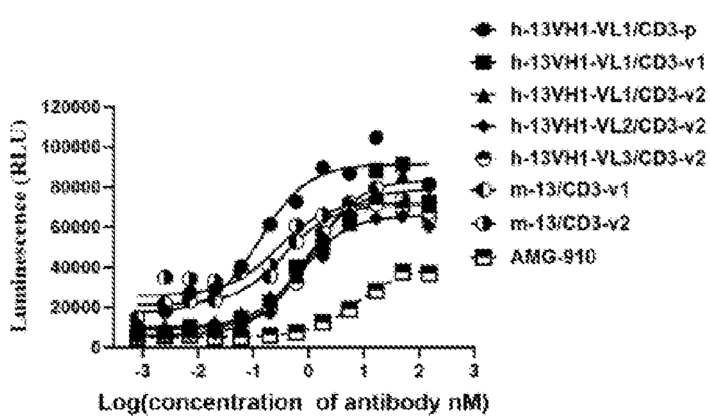
Fig.15

CLDN18.2/CD3 BISPECIFIC ANTIBODIES FOR THE THERAPY OF CLDN18.2-EXPRESSING SOLID TUMORS

This application is a National Stage application under 35 U.S.C. § 371 of International Application No. PCT/CN2022/075326, having an International Filing Date of Feb. 7, 2022, which claims the benefit of U.S. Provisional Patent Application No. 63/147,233, entitled "CLDN18.2/CD3 bispecific antibodies for the therapy of CLDN18.2-expressing solid tumors", filed on Feb. 8, 2021, the content of which is herein incorporated by reference in its entirety.

SEQUENCE LISTING

This application contains a Sequence Listing that has been submitted electronically as an ASCII text file named "48644-0014US1.txt." The ASCII text file, created on Feb. 7, 2022 is 42,076 bytes in size. The material in the ASCII text file is hereby incorporated by reference in its entirety.

TECHNICAL FIELD

The present application relates to CLDN18.2 antibodies or antigen binding fragments thereof and related CLDN18.2/CD3 bispecific antibodies, as well as corresponding nucleic acids encoding same, vectors comprising such nucleic acids, host cells transfected with such nucleic acids or vectors. The present application further relates to isolated CLDN18.2 antibodies or antigen binding fragments thereof and related CLDN18.2/CD3 bispecific antibodies, pharmaceutical compositions comprising such antibodies, antigen binding fragments, bispecific antibodies, nucleic acids, vectors, or host cells and optionally a pharmaceutically acceptable carrier, and methods of treating cancer in a subject in need thereof by administering such pharmaceutical compositions. The cancers treated in accordance with the present application include CLDN18.2-positive cancers, such as, inter alia, gastric cancer and pancreatic cancer.

BACKGROUND

CLDN18.2 protein is a transmembrane protein, which belongs to the Claudins (CLDNs) family. The entire protein is expressed on the cell membrane and is an important structural component of the tight junction of cells. Claudins have 4 transmembrane regions, 2 extracellular loops and 1 intracytoplasmic loop, which participate in the formation of tight junctions between cells. There are two alleles in the first exon of human CLDN18 gene, which can express two different splicing mutants known as CLDN18.1 and CLDN18.2, resulting in a 69 amino acid sequence at the N-terminal including extracellular loop 1. Therefore, there are differences between the two extracellular epitopes. Although most CLDNs are widely expressed, individual members are often highly selectively expressed in specific tissues.

Among them, CLDN18.1 protein is a specific antigen selectively expressed by alveolar epithelial cells, which is only highly expressed in normal alveolar tissues, but not found in other normal tissues, including pancreatic ducts; CLDN18.2 protein is also a highly selective marker protein, but its distribution is completely different than CLDN18.1 protein. The expression of CLDN18.2 protein is highly restricted in normal healthy tissues. It is not expressed in undifferentiated gastric stem cells. It is only expressed in differentiated gastric mucosal membrane epithelial cells, and the expression level is very limited. This is conducive to maintaining the gastric mucosa, whose barrier function can prevent H+ in gastric acid from leaking through paracellular pathways. However, CLDN18.2 protein frequently undergoes abnormal changes during the development of a variety of malignant tumors. For example, when gastric epithelial tissue undergoes malignant transformation, the resultant disorder of cell polarity will cause the CLDN18.2 protein epitope on the cell surface to be exposed. At the same time, CLDN18.2 gene will also be abnormally activated, and highly selectively and stably expressed in specific tumor tissues involved in the proliferation, differentiation, and migration of tumor cells.

In recent years, CLDN18.2 has become a promising target for tumor therapy. So far, nearly 20 innovative pharmaceutical companies have deployed CLDN18.2-targeted drug development. Most of these research projects are single-target antibody drugs. Among them, CLDN18.2 specific antibody Claudiximab (Zolbetuximab/IMAB362) has achieved remarkable success in clinical trials. A phase II study from Europe showed that compared with chemotherapy alone, the overall survival time of patients with advanced gastric cancer was extended from 8.4 months to 13.2 months after treatment with IMAB362 and standard chemotherapy. In this study, patients with the highest claudin 18.2 levels had a longer median overall survival time (16.7 months). Moreover, CLDN18.2 double-antibody drugs have also ushered in exciting new developments in solid tumor therapy. Recently, a new CLDN18.2/CD3 bispecific antibody, AMG 910, has been approved for Phase I clinical trials for gastric cancer and gastroesophageal junction cancer.

Overall, the evidence from current clinical trials has demonstrated that CLDN18.2 antibodies have high safety, tolerability, and anti-tumor activity as a targeted drug for patients with CLDN18.2-positive advanced gastric cancer.

SUMMARY OF THE INVENTION

The present application provides novel CLDN18.2 antibodies or antigen binding fragments thereof and also related bispecific antibodies with particularly advantageous properties such as high producibility, stability, binding affinity, biological activity, specific targeting of CLDN18.2-positive cells, targeting efficiency, remaining tumor cell killing and/or reduced toxicity.

In one aspect, the present application provides a CLDN18.2 antibody or antigen binding fragment thereof, comprising a heavy chain variable region and a light chain variable region, the heavy chain variable region comprises HCDR1 comprising the amino acid sequence represented by SEQ ID NO. 11, HCDR2 comprising the amino acid sequence represented by SEQ ID NO. 12 and HCDR3 comprising the amino acid sequence represented by SEQ ID NO. 13, and/or the light chain variable region comprises LCDR1 comprising the amino acid sequence represented by SEQ ID NO. 14, LCDR2 comprising the amino acid sequence represented by SEQ ID NO. 15 and LCDR3 comprising the amino acid sequence represented by SEQ ID NO. 16.

In another aspect of the present application, the antigen binding fragment is selected from scFv fragment, Fv fragment, F(ab')2 fragment, Fab' —SH fragment and Fab' fragment.

In a further aspect, the CLDN18.2 antibody or antigen binding fragment binds to CLDN 18.2, and does not bind to CLDN 18.1.

In a further aspect, the above-mentioned antibody is a monoclonal antibody or a humanized antibody.

In a further aspect, such monoclonal antibody or humanized antibody includes antibodies produced by hybridomas or host cells transformed with an expression vector modified to carry an antibody gene by genetic engineering techniques. In a further embodiment, the monoclonal antibody or humanized antibody may comprise IgG antibodies comprising two heavy chains and two light chains; heavy chains of mouse IgG antibodies are classified into five subclasses according to the constant region of their heavy chains: IgG1, IgG2a, IgG2b, IgG2c and IgG3, and the light chains may be mouse lambda or kappa type; and heavy chains of human IgG antibodies are further classified into four subclasses according to the constant region of their heavy chains: IgG1, IgG2, IgG3, and IgG4, and the light chains may be human lambda or kappa type.

In a further aspect, the disclosure also provides a monoclonal CLDN18.2 antibody including a light chain variable region and a heavy chain variable region, wherein the heavy chain variable region comprises an amino acid sequence with at least 95%, 96%, 97%, 98%, 99% or 100% sequence identity to the sequence of SEQ ID NO. 1, and/or the light chain variable region comprises an amino acid sequence with at least 95%, 96%, 97%, 98%, 99% or 100% sequence identity to the sequence of SEQ ID NO. 2.

In a further aspect, the disclosure also provides a monoclonal CLDN18.2 antibody including a light chain variable region and a heavy chain variable region, wherein the heavy chain variable region comprises an amino acid sequence with at least 95%, 96%, 97%, 98%, 99% or 100% sequence identity to the sequence of SEQ ID NO. 3, and/or the light chain variable region comprises an amino acid sequence with at least 95%, 96%, 97%, 98%, 99% or 100% sequence identity to the sequence of SEQ ID NO. 4.

In a further aspect, the disclosure also provides a monoclonal CLDN18.2 antibody including a light chain variable region and a heavy chain variable region, wherein the heavy chain variable region comprises an amino acid sequence with at least 95%, 96%, 97%, 98%, 99% or 100% sequence identity to the sequence of SEQ ID NO. 5, and/or the light chain variable region comprises an amino acid sequence with at least 95%, 96%, 97%, 98%, 99% or 100% sequence identity to the sequence of SEQ ID NO. 6.

In a further aspect, the disclosure also provides a monoclonal CLDN18.2 antibody including a light chain variable region and a heavy chain variable region, wherein the heavy chain variable region comprises an amino acid sequence with at least 95%, 96%, 97%, 98%, 99% or 100% sequence identity to the sequence of SEQ ID NO. 7, and/or the light chain variable region comprises an amino acid sequence with at least 95%, 96%, 97%, 98%, 99% or 100% sequence identity to the sequence of SEQ ID NO. 8.

In a further aspect, the disclosure also provides a monoclonal CLDN18.2 antibody including a light chain variable region and a heavy chain variable region, wherein the heavy chain variable region comprises an amino acid sequence with at least 95%, 96%, 97%, 98%, 99% or 100% sequence identity to the sequence of SEQ ID NO. 9, and/or the light chain variable region comprises an amino acid sequence with at least 95%, 96%, 97%, 98%, 99% or 100% sequence identity to the sequence of SEQ ID NO. 10.

In a further aspect, the antibody or antigen-binding fragment thereof is a humanized antibody or antigen-binding fragment thereof, wherein the humanized CLDN18.2 antibody includes a light chain variable region and a heavy chain variable region, wherein the heavy chain variable region comprises an amino acid sequence with at least 95%, 96%, 97%, 98%, 99% or 100% sequence identity to the sequence of any one of SEQ ID NOs. 17-21, and/or the light chain variable region comprises an amino acid sequence with at least 95%, 96%, 97%, 98%, 99% or 100% sequence identity to the sequence of any one of SEQ ID NOs. 22-24.

In a further aspect, the antibody or antigen-binding fragment thereof is a humanized antibody or antigen-binding fragment thereof, the humanized CLDN18.2 antibody includes a light chain variable region and a heavy chain variable region, wherein the heavy chain variable region comprises an amino acid sequence with at least 95%, 96%, 97%, 98%, 99% or 100% sequence identity to the sequence of SEQ ID NO. 17, and the light chain variable region comprises an amino acid sequence with at least 95%, 96%, 97%, 98%, 99% or 100% sequence identity to the sequence of SEQ ID NO. 22.

In a further embodiment, the antibody comprises a light chain constant domain, and optionally a heavy chain constant domain.

Optionally, the heavy chain constant domain is a human IgG1 heavy chain constant domain, or the light chain constant domain is a human kappa light chain constant domain. In a further embodiment, the heavy chain constant domain may contain one or more mutations, for example, mutations L234A, L235A and P329A, that reduce or eliminate an effect of ADCC and/or CDC.

In a specific aspect, the present application provides a CD3 antigen binding domain that specifically binds to CD3, wherein the antigen binding fragment comprises a heavy chain variable region and a light chain variable region, wherein the heavy chain variable region comprises HCDR1 comprising the amino acid sequence represented by SEQ ID NO. 31, HCDR2 comprising the amino acid sequence represented by SEQ ID NO. 32 and HCDR3 comprising the amino acid sequence represented by SEQ ID NO. 33, and/or the light chain variable region comprises LCDR1 comprising the amino acid sequence represented by SEQ ID NO. 34, LCDR2 comprising the amino acid sequence represented by SEQ ID NO. 35 and LCDR3 comprising the amino acid sequence represented by SEQ ID NO. 36;

the heavy chain variable region comprises HCDR1 comprising the amino acid sequence represented by SEQ ID NO. 37, HCDR2 comprising the amino acid sequence represented by SEQ ID NO. 38 and HCDR3 comprising the amino acid sequence represented by SEQ ID NO. 39, and/or the light chain variable region comprises LCDR1 comprising the amino acid sequence represented by SEQ ID NO. 34, LCDR2 comprising the amino acid sequence represented by SEQ ID NO. 35 and LCDR3 comprising the amino acid sequence represented by SEQ ID NO. 36; or the heavy chain variable region comprises HCDR1 comprising the amino acid sequence represented by SEQ ID NO. 37, HCDR2 comprising the amino acid sequence represented by SEQ ID NO. 40 and HCDR3 comprising the amino acid sequence represented by SEQ ID NO. 39, and/or the light chain variable region comprises LCDR1 comprising the amino acid sequence represented by SEQ ID NO. 34, LCDR2 comprising the amino acid sequence represented by SEQ ID NO. 35 and LCDR3 comprising the amino acid sequence represented by SEQ ID NO. 36.

In a specific aspect, the present application provides a CD3 antigen binding domain that specifically binds to CD3, wherein the antigen binding fragment comprises a heavy chain variable region (VH domain) and a light chain variable region (VL domain) wherein:

the heavy chain variable region comprises an amino acid sequence with at least 95%, 96%, 97%, 98%, 99% or 100% sequence identity to the sequence of SEQ ID NO. 25, and the light chain variable region comprises an amino acid sequence with at least 95%, 96%, 97%, 98%, 99% or 100% sequence identity to the sequence of SEQ ID NO. 26; or the heavy chain variable region comprises an amino acid sequence with at least 95%, 96%, 97%, 98%, 99% or 100% sequence identity to the sequence of SEQ ID NO. 27, and the light chain variable region comprises an amino acid sequence with at least 95%, 96%, 97%, 98%, 99% or 100% sequence identity to the sequence of SEQ ID NO. 26; or the heavy chain variable region comprises an amino acid sequence with at least 95%, 96%, 97%, 98%, 99% or 100% sequence identity to the sequence of SEQ ID NO. 28, and the light chain variable region comprises an amino acid sequence with at least 95%, 96%, 97%, 98%, 99% or 100% sequence identity to the sequence of SEQ ID NO. 26.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof.

In a further aspect, in the above-mentioned bispecific antibody, the first antibody or antigen binding fragment thereof is the above-mentioned CLDN18.2 antibody or antigen binding fragment thereof, and the second antigen binding domain is the above-mentioned CD3 antigen binding domain.

In a further aspect, in the above-mentioned bispecific antibody, the first antibody or antigen binding fragment thereof comprises two identical heavy chain and two identical light chains, and the second antigen binding domain comprises two identical single chain antibody fragments (scFv).

In a further aspect, in the above-mentioned bispecific antibody, each of the light chains of the first antibody or antigen binding fragment is fused to each said single chain antibody fragment (scFv) of the second antigen binding domain.

In a further aspect, in the above-mentioned bispecific antibody, the C-terminal of the constant region of each said light chain of the first antibody or antigen binding fragment is fused to the N-terminal of the heavy chain variable region of each said single chain antibody fragment (scFv) of the second antigen binding domain, directly or via a peptide linker.

In a further aspect, the above-mentioned bispecific antibody comprises a monoclonal antibody that is an immunoglobulin that binds to CLDN18.2, said immunoglobulin comprising two identical heavy chains and two identical light chains, wherein said light chains are a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical.

In one specific aspect, in the above-mentioned bispecific antibody, the C-terminal of the constant region of the first light chain is fused to the N-terminal of the heavy chain variable region of the first scFv directly or via a peptide linker, and the C-terminal of the constant region of the second light chain is fused to the N-terminal of the heavy chain variable region of the second scFv directly or via a peptide linker.

In one specific aspect, in the above-mentioned bispecific antibody, each of the first and second scFv comprises the above mentioned CD3 antigen binding domain.

In a specific aspect, the above-mentioned bispecific antibody provided herein binds to both CLDN18.2 and CD3.

In a specific aspect, the sequence of the above-mentioned peptide linker is shown in SEQ ID NO. 41 or SEQ ID NO. 42.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof, wherein a first antibody or antigen binding fragment thereof includes a light chain variable region and a heavy chain variable region, wherein the heavy chain variable region comprises HCDR1 comprising the amino acid sequence represented by SEQ ID NO. 11, HCDR2 comprising the amino acid sequence represented by SEQ ID NO. 12 and HCDR3 comprising the amino acid sequence represented by SEQ ID NO. 13, and the light chain variable region comprises LCDR1 comprising the amino acid sequence represented by SEQ ID NO. 14, LCDR2 comprising the amino acid sequence represented by SEQ ID NO. 15 and LCDR3 comprising the amino acid sequence represented by SEQ ID NO. 16; and the second antigen binding domain comprises a heavy chain variable region and a light chain variable region, wherein the heavy chain variable region comprises HCDR1 comprising the amino acid sequence represented by SEQ ID NO. 31, HCDR2 comprising the amino acid sequence represented by SEQ ID NO. 32 and HCDR3 comprising the amino acid sequence represented by SEQ ID NO. 33, and the light chain variable region comprises LCDR1 comprising the amino acid sequence represented by SEQ ID NO. 34, LCDR2 comprising the amino acid sequence represented by SEQ ID NO. 35 and LCDR3 comprising the amino acid sequence represented by SEQ ID NO. 36.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof, wherein a first antibody or antigen binding fragment thereof includes a light chain variable region and a heavy chain variable region, wherein the heavy chain variable region comprises HCDR1 comprising the amino acid sequence represented by SEQ ID NO. 11, HCDR2 comprising the amino acid sequence represented by SEQ ID NO. 12 and HCDR3 comprising the amino acid sequence represented by SEQ ID NO. 13, and the light chain variable region comprises LCDR1 comprising the amino acid sequence represented by SEQ ID NO. 14, LCDR2 comprising the amino acid sequence represented by SEQ ID NO. 15 and LCDR3 comprising the amino acid sequence represented by SEQ ID NO. 16; and the second antigen binding domain comprises a heavy chain variable region and a light chain variable region, wherein the heavy chain variable region comprises HCDR1 comprising the amino acid sequence represented by SEQ ID NO. 37, HCDR2 comprising the amino acid sequence represented by SEQ ID NO. 38 and HCDR3 comprising the amino acid sequence represented by SEQ ID NO. 39, and the light chain variable region comprises LCDR1 comprising the amino acid sequence represented by SEQ ID NO. 34, LCDR2 comprising the amino acid sequence represented by SEQ ID NO. 35 and LCDR3 comprising the amino acid sequence represented by SEQ ID NO. 36.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof, wherein a first antibody or antigen binding fragment thereof includes a light chain variable region and a heavy chain variable region, wherein the heavy chain variable region comprises HCDR1 comprising the amino acid sequence represented by SEQ ID NO. 11, HCDR2 comprising the amino acid sequence represented by SEQ ID NO. 12 and HCDR3 comprising the amino acid sequence represented by SEQ ID NO. 13, and the light chain variable region comprises LCDR1 comprising the amino acid sequence represented by SEQ ID NO. 14, LCDR2 comprising the amino acid sequence represented by SEQ ID NO. 15 and LCDR3 comprising the amino acid sequence represented by SEQ ID NO. 16; and the second antigen binding domain comprises a heavy chain variable region and a light chain variable region, wherein the heavy chain variable region comprises HCDR1 comprising the amino acid sequence represented by SEQ ID NO. 37, HCDR2 comprising the amino acid sequence represented by SEQ ID NO. 40 and HCDR3 comprising the amino acid sequence represented by SEQ ID NO. 39, and the light chain variable region comprises LCDR1 comprising the amino acid sequence represented by SEQ ID NO. 34, LCDR2 comprising the amino acid sequence represented by SEQ ID NO. 35 and LCDR3 comprising the amino acid sequence represented by SEQ ID NO. 36.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof, wherein a first antibody or antigen binding fragment thereof includes a light chain variable region and a heavy chain variable region, wherein the heavy chain variable region comprises an amino acid sequence with at least 95%, 96%, 97%, 98%, 99% or 100% sequence identity to the sequence of SEQ ID NO. 17, and the light chain variable region comprises an amino acid sequence with at least 95%, 96%, 97%, 98%, 99% or 100% sequence identity to the sequence of SEQ ID NO. 22; and the second antigen binding domain comprises a heavy chain variable region and a light chain variable region, wherein the heavy chain variable region comprises an amino acid sequence with at least 95%, 96%, 97%, 98%, 99% or 100% sequence identity to the sequence of SEQ ID NO. 25, and the light chain variable region comprises an amino acid sequence with at least 95%, 96%, 97%, 98%, 99% or 100% sequence identity to the sequence of SEQ ID NO. 26.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof, wherein a first antibody or antigen binding fragment thereof includes a light chain variable region and a heavy chain variable region, wherein the heavy chain variable region comprises an amino acid sequence with at least 95%, 96%, 97%, 98%, 99% or 100% sequence identity to the sequence of SEQ ID NO. 17, and the light chain variable region comprises an amino acid sequence with at least 95%, 96%, 97%, 98%, 99% or 100% sequence identity to the sequence of SEQ ID NO. 22; and the second antigen binding domain comprises a heavy chain variable region and a light chain variable region, wherein the heavy chain variable region comprises an amino acid sequence with at least 95%, 96%, 97%, 98%, 99% or 100% sequence identity to the sequence of SEQ ID NO. 27, and the light chain variable region comprises an amino acid sequence with at least 95%, 96%, 97%, 98%, 99% or 100% sequence identity to the sequence of SEQ ID NO. 26.

In a further aspect, the present application provides a bispecific antibody, comprising a first antibody or antigen binding fragment thereof that specifically binds to CLDN18.2 or a naturally occurring variant thereof and a second antigen binding domain that specifically binds to CD3 or a naturally occurring variant thereof, wherein a first antibody or antigen binding fragment thereof includes a light chain variable region and a heavy chain variable region, wherein the heavy chain variable region comprises an amino acid sequence with at least 95%, 96%, 97%, 98%, 99% or 100% sequence identity to the sequence of SEQ ID NO. 17, and the light chain variable region comprises an amino acid sequence with at least 95%, 96%, 97%, 98%, 99% or 100% sequence identity to the sequence of SEQ ID NO. 22; and the second antigen binding domain comprises a heavy chain variable region and a light chain variable region, wherein the heavy chain variable region comprises an amino acid sequence with at least 95%, 96%, 97%, 98%, 99% or 100% sequence identity to the sequence of SEQ ID NO. 28, and the light chain variable region comprises an amino acid sequence with at least 95%, 96%, 97%, 98%, 99% or 100% sequence identity to the sequence of SEQ ID NO. 26.

In a further aspect, the above-mentioned bispecific antibodies provided herein have advantageous properties such as high producibility, stability, binding affinity, biological activity, specific targeting of certain T cells, targeting efficiency, remaining tumor cell killing and reduced toxicity.

In a further aspect, the above-mentioned bispecific antibody provided here shows reduced binding affinity with CD3 compared to wild-type CD3 binders.

In a further aspect, the above-mentioned bispecific antibodies provided herein show reduced TCR signaling strength.

In a further aspect, the above-mentioned bispecific antibodies provided herein show reduced cytokine release mediated by mutant CD3 binder variants.

In a further aspect, the present application also provides an isolated nucleic acid comprising nucleic acid sequences encoding the above-described CLDN18.2 antibody or antigen binding fragment thereof or the above-mentioned bispecific antibody.

In a further aspect, the present application also provides a vector comprising the nucleic acid encoding the above-mentioned CLDN18.2 antibody or antigen binding fragments thereof or the above-mentioned bispecific antibody.

In a further aspect, the disclosure also provides an isolated host cell comprising the above-mentioned vector or the above-mentioned isolated nucleic acid.

The appropriate host cells are transformed with the above-mentioned vector, and the above-mentioned host cells expressing the above-mentioned CLDN18.2 antibody or antigen binding fragments thereof or the above-mentioned bispecific antibody are obtained.

In a further aspect, the disclosure also provides various known host cell/expression vector combinations for antibody preparation by introducing isolated antibody genes into appropriate hosts. Appropriate eukaryotic cells used as host cells include animal cells, plant cells, and fungal cells. Specifically, the animal cells include, for example, the following cells: (1) mammalian cells: CHO, COS, myeloma, baby hamster kidney (BHK), HeLa, Vero, or such; (2) amphibian cells: *Xenopus* oocytes, or such; and (3) insect cells: sf9, sf21, Tn5, or such.

In a further aspect, the disclosure also provides a method of producing the above-mentioned antibody or antigen binding fragment thereof or the above-mentioned bispecific antibody, comprising culturing the above-mentioned host cell so that the antibody or antigen binding fragment thereof or the bispecific antibody is produced. In a further aspect, the method further comprises recovering the antibody or antigen binding fragment thereof or the bispecific antibody produced by the host cell.

In a further aspect, the disclosure also provides the isolated antibody or antigen binding fragment thereof or the bispecific antibody produced by the above-mentioned method.

In a further aspect, the disclosure also provides a pharmaceutical composition comprising the above-mentioned CLDN18.2 antibody or antigen binding fragment thereof or the above-mentioned bispecific antibody, nucleic acid, vector, the host cell and optionally a pharmaceutically acceptable carrier.

In a further aspect, the disclosure also provides a method of treating cancer in a subject in need thereof, comprising administering to the subject the above-mentioned pharmaceutical composition comprising the above-mentioned CLDN18.2 antibody or antigen binding fragment thereof or the above-mentioned bispecific antibody, nucleic acid, vector, the host cell and optionally a pharmaceutically acceptable carrier.

In a further aspect, the above-mentioned cancer is a CLDN18.2-positive cancer.

In a further aspect, the cancer is hematological cancer or solid cancer.

In a further aspect, the CLDN18.2-positive cancer includes but is not limited to gastric cancer or pancreatic cancer.

The technical solutions of the present application have one or more of the following advantages:

1. The CLDN18.2 antibody or antigen binding fragments are highly selective and specific to CLDN18.2; the antibodies have particularly advantageous properties such as high producibility, stability, binding affinity, biological activity, specific targeting of CLDN18.2-positive cells, efficient TCR signaling strength, targeting efficiency, remaining tumor cell killing and reduced cytotoxicity.
2. The above-mentioned bispecific antibodies provided herein have advantageous properties such as high producibility, stability, binding affinity, biological activity, specific targeting of certain T cells, targeting efficiency, remaining tumor cell killing and reduced toxicity.
3. The above-mentioned bispecific antibody with mutant CD3 binders provided herein shows reduced binding affinity with CD3, and reduced cytokines release mediated by mutant CD3 binder variants compared to bispecific antibody with wild-type CD3 binders.
4. The application enables desirable treatment for cancer which has not only a high level of safety but also reduced physical burden, and is highly convenient for patients.

BRIEF DESCRIPTION OF THE DRAWINGS

The novel features of the present application are set forth with particularity in the appended claims. Some of the features and advantages of the present application are explained in the following detailed description in the embodiments and in the examples.

FIG. 5A-5F. Comparison of killing activity mediated by murine CLDN18.2/CD3 bispecific antibodies against target cells with various expression levels of CLDN18.2. CLDN18.2 overexpressing HEK (i.e. CLDN18.2$^+$HEK or CLDN18.2 overexpressing HEK293) (FIG. 5A), medium CLDN18.2 expressing SNU620 (FIG. 5B) and low CLDN18.2 expressing KATO III (FIG. 5C) target cells were harvested, counted and seeded in 96-well plates. Effector PBMCs were added to each well in a proportion of 20:1 in RPMI 1640. Serial dilutions of the indicated antibodies were performed in RPMI 1640 medium and added to the target/effector-containing well. The plates were incubated for 48 hours, and Luciferase intensity was determined. FIG. 5D-5F shows EC50 of killing potency for murine CLDN18.2/CD3 bispecific antibodies.

FIG. 13. Comparable killing activity mediated by humanized CLDN18.2/CD3 and murine CLDN18.2-13/CD3 bispecific antibodies. CLDN18.2-expressing SNU620 and CLDN18.2-overexpressing HEK cells were harvested, counted and seeded in 96-well plates. Effector PBMCs were added to each well in a proportion of 20:1 in serial dilutions of VL1+VH1-5 (the top left panel), VL1+VH1-5 (the top right panel), VL3+HV1-5 (the bottom left panel), and VL3+VL1-5 (the bottom right panel) bispecific antibodies. The plates were incubated for 48 hours, and Luciferase intensity was determined.

FIG. 14A-14D. Comparison of binding affinity of humanized CLDN18.2/CD3 bispecific antibodies with murine parental CLDN18.2-13/CD3 bispecific antibody. CLDN18.2-expressing SNU620 cells (FIG. 14A) and Jurkat cells (FIG. 14C) were stained with h-13/CD3, m-13/CD3, Amgen CLDN18.2/CD3 bispecific antibodies or IgG control, followed by a PE-conjugated anti-human IgG ab. Mean fluorescence intensity (MFI) was determined by flow cytometry. FIG. 14B and FIG. 14D shows EC50 of binding affinity of humanized CLDN18.2/CD3 bispecific antibodies with murine parental CLDN18.2-13/CD3 bispecific antibody.

FIG. 15. Comparison of TCR-NFAT signaling mediated by CLDN18.2-13/CD3 bispecific antibodies. NFAT reporter Jurkat cells were cocultured with CLDN18.2-expressing SNU620 cells (E/T: 3/1) in serial dilutions of h-13/CD3, m-13/CD3, AMG-910 for 6 hours. NFAT activity was determined by relative luminescence units (RLU).

DETAILED DESCRIPTION OF THE INVENTION

Figure 1:
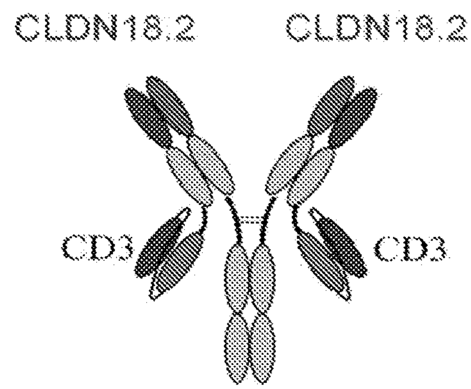
FIG. 1 shows an illustration of CLDN18.2/CD3 bispecific antibody structure. Each anti-CD3 single-chain variable fragment (scFv) is linked to the C-terminus of an anti-CLDN18.2 light chain. The anti-CD3 sequence contains key point mutations (L234A, L235A and P329A) that abrogate binding of Fcγ receptors (FcγR), abolishing antibody directed cytotoxicity (ADCC) and complement-dependent cytotoxicity (CDC) effector functions.

Unless defined otherwise, technical and scientific terms used herein have the same meaning as generally used in the art to which this disclosure belongs. For purposes of interpreting this specification, the following definitions will apply and whenever appropriate, terms used in the singular will also include the plural and vice versa. As used herein and in the appended claims, the singular forms “a”, “an”, and “the” also refer to the plural forms unless the context clearly dictates otherwise, e.g., reference to “a host cell” includes a plurality of such host cells.

As used herein, the term “antigen binding fragment” or “antigen binding molecule” refers in its broadest sense to a molecule that specifically binds an antigenic determinant. Examples of antigen binding molecules are antibodies, antibody fragments and scaffold antigen binding proteins. The term “antibody” herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term “antibody” as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

A humanized antibody is also called a reshaped human antibody. Specifically, humanized antibodies prepared by grafting the CDR of a non-human animal antibody such as a mouse antibody to a human antibody are known in the art. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

The term "bispecific" means that the antibody is able to specifically bind to at least two distinct antigenic determinants, for example two binding sites each formed by a pair of an antibody heavy chain variable domain (VH) and an antibody light chain variable domain (VL) binding to different antigens or to different epitopes on the same antigen. Such a bispecific antibody is referred to as a 1+1 format. Other bispecific antibody formats are 2+1 formats (comprising two binding sites for a first antigen or epitope and one binding site for a second antigen or epitope) or 2+2 formats (comprising two binding sites for a first antigen or epitope and two binding sites for a second antigen or epitope). Typically, a bispecific antibody comprises two antigen binding sites, each of which is specific for a different antigenic determinant. The term "valent" as used within the current application denotes the presence of a specified number of binding domains in an antigen binding molecule. As such, the terms "bivalent", "tetravalent", and "hexavalent" denote the presence of two binding domains, four binding domains, and six binding domains, respectively, in an antigen binding molecule. The bispecific antibodies according to the disclosure are at least "bivalent" and may be "trivalent" or "multivalent" (e.g., "tetravalent" or "hexavalent"). In a particular aspect, the antibodies of the present disclosure have two or more binding sites and are bispecific. That is, the antibodies may be bispecific even in cases where there are more than two binding sites (i.e. that the antibody is trivalent or multivalent). The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are hetero-tetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g., γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain. An "antibody fragment" refers to a molecule other than an intact antibody that comprises a portion of an intact antibody that binds the antigen to which the intact antibody binds. Examples of antibody fragments include but are not limited to Fv, Fab, Fab', Fab' —SH, F(ab')2; diabodies, triabodies, tetrabodies, cross-Fab fragments; linear antibodies; single-chain antibody molecules (e.g., scFv); multispecific antibodies formed from antibody fragments and single domain antibodies. Single-domain antibodies are antibody fragments comprising all or a portion of the heavy chain variable domain or all or a portion of the light chain variable domain of an antibody. In certain embodiments, a single-domain antibody is a human single-domain antibody. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full-length antibodies. Antibody fragments can be made by various techniques, including but not limited to proteolytic digestion of an intact antibody as well as production by recombinant host cells (e.g., *E. coli* or phage), as described herein. Papain digestion of intact antibodies produces two identical antigen-binding fragments, called "Fab" fragments, each containing the heavy- and light-chain variable domains and also the constant domain of the light chain and the first constant domain (CH1) of the heavy chain. As used herein, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteines from the antibody hinge region. Fab' —SH are Fab' fragments wherein the cysteine residue(s) of the constant domains bear a free thiol group. Pepsin treatment yields an F(ab')2 fragment that has two antigen-combining sites (two Fab fragments) and a part of the Fc region.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. In addition, antibody fragments comprising single chain polypeptides have the characteristics of a VH domain, namely being able to assemble together with a VL domain, or of a VL domain, namely being able to assemble together with a VH domain to a functional antigen binding site, thereby providing the antigen binding properties of full-length antibodies.

By "specific binding" it is meant that the binding is selective for the antigen and can be distinguished from unwanted or non-specific interactions with substrates other than the antigen. The ability of an antigen binding molecule to bind to a specific antigen can be measured either through an enzyme-linked immunosorbent assay (ELISA) or other techniques familiar to one of skill in the art, and traditional binding assays. In one embodiment of the present application, the extent of binding of an antigen binding molecule to an unrelated protein is less than about 10% of the binding of the antigen binding molecule to the antigen as measured, e.g., by SPR. In certain embodiments, a molecule that binds to the antigen has a dissociation constant (Kd) of <1 μM, <100 nM, <10 nM, <1 nM, <0.1 nM, <0.01 nM, or <0.001 nM (e.g., 10-7 M or less, e.g., from 10-7 M to 10-13 M, e.g., from 10-9 M to 10-13 M).

"Affinity" or "binding affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR). As used herein, the term "high affinity" of an antibody refers to an antibody having a Kd of $10^{-9}$ M or less and even more particularly $10^{-10}$ M or less for a target antigen. The term "low affinity" of an antibody refers to an antibody having a Kd of $10^{-8}$ or higher.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). A single VH or VL domain may be sufficient to confer antigen-binding specificity.

Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services. Unless otherwise specified, references to the numbering of specific amino acid residue positions in an antibody variable region herein are made according to the Kabat numbering system. With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. Unless otherwise indicated, HVR residues and other residues in the variable domain (e.g., FR residues) are numbered herein according to Kabat et al.

By "fused to" or "connected to", it is meant that the components (e.g., an antigen binding domain and a FC domain) are linked by peptide bonds, either directly or via one or more peptide linkers.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages.

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent, for example, eliminates, decreases, delays, minimizes or prevents adverse effects of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human. The term "pharmaceutical composition" refers to a preparation which is in such form as to permit the biological activity of an active ingredient contained therein to be effective, and which contains no additional components which are unacceptably toxic to a subject to which the formulation would be administered. A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the present application are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewing's sarcoma, including refractory versions of any of the above cancers, or a combination of one or more of the above cancers.

Definitions

For purposes of interpreting the antibodies used in the following examples, the following definitions are provided.

1. Definition of anti-CLDN18.2 monoclonal antibodies used in the following examples:
   1) 2 lead humanized CLDN18.2 antibodies: hCLDN18.2 841 (i.e. h841), hCLDN18.2 808 (i.e. h808), and sequences thereof are shown in Table 1;
   2) 3 lead murine anti-human CLDN18.2 antibodies: m-anti-human CLDN18.2-6 (i.e. m-6), m-anti-human CLDN18.2-12 (i.e. m-12), and m-anti-human CLDN18.2-13 (i.e. m-13), and sequences thereof are shown in Table 1;
   3) humanized m-13: h-13, and VH and VL thereof are shown in Table 2;
   4) humanized m-6: h-6, and VH and VL thereof are shown in Table 2-1.
2. Definition of anti-CD3 antibody used in the following examples:
   1) humanized anti-CD3 antibody: SP34(i.e. CD3-p or CD3 Parental, mutant CD3 antibody (CD3-v1, CD3-v2); and the sequences thereof are shown in Table 3;
3. Definition of anti-CLDN18.2/CD3 BsAbs used in the following examples:
   1) CLDN18.2/CD3 bsAbs:

①h808/CD3-p, h841/CD3-p, m-6/CD3-p, m-13/CD3-p;

②h841/CD3-v1, h841/CD3-v2;

2) CLDN18.2/CD3 bsAbs using humanized m-13, that is, CLDN18.2-13/CD3 bispecific antibodies or h-13/CD3 bsAbs:

①CLDN18.2-13/CD3 bispecific antibodies (i.e. h-13/CD3 bsAbs) with CD3-p (i.e. CD3 Parental) arm (i.e. 15 humanized CLDN18.2-13/CD3 bispecific antibodies):

h-13VH1-VL1/CD3-p, h-13VH2-VL1/CD3-p, h-13VH3-VL1/CD3-p, h-13VH4-VL1/CD3-p, h-13VH5-VL1/CD3-p, h-13VH1-VL2/CD3-p, h-13VH2-VL2/CD3-p, h-13VH3-VL2/CD3-p, h-13VH4-VL2/CD3-p, h-13VH5-VL2/CD3-p, h-13VH1-VL3/CD3-p, h-13VH2-VL3/CD3-p, h-13VH3-VL3/CD3-p, h-13VH4-VL3/CD3-p, h-13VH5-VL3/CD3-p,

②CLDN18.2-13/CD3 bispecific antibodies (i.e. h-13/CD3 bsAbs) with mutant CD3 arm (CD3-v1 or CD3-v2):

h-13VH1-VL1/CD3-v1, h-13VH1-VL1/CD3-v2, h-13VH1-VL2/CD3-v2, and hVH1-VL3/CD3-v2

3) Benchmark bispecific antibody: AMG-910.

TABLE 1

The VH or VL sequence of the anti-CLDN18.2 monoclonal antibodies (Underlined Sequences represent CDRs, the analysis system is Kabat system)

| Clones | Heavy Chain (VH) | Light Chain (VL) |
|---|---|---|
| hCLDN18.2 841 | QVQLVQSGAEVKKPGSSVKVSCK ASGGTFSSYAISWVRQAPGQGLEW MGRIIPILGIANYAQKFQGRVTVTA DKSTSTAYMELSSLRSEDTAVYYC ARERDNWDPYYYYYGMDVWGQ GTTVTVSS (SEQ ID NO. 1) | DIQMTQSPSTLSASVGDRVTITCRA SQSINSWLAWYQQKPGKAPKLLIY KASSLESGVPSRFSGSGSGTEFTLTI SSLQPDDFATYYCQQYNSFPLTFGG GTKVEIK (SEQ ID NO. 2) |
| hCLDN18.2 808 | EVQLVQSGGGVVQPGRSLRLSCA ASGFTFSSYAMHWVRQAPGKGLE WVAVISYDGSNKYYADSVKGRFTI SRDNSKNTLYLQMNSLRAEDTAV YYCARELRFFDWLLGSAFDIWGQ GTTVTVSS (SEQ ID NO. 3) | DIVMTQSPSSLSASVGDRVTITCRA SQGIRNDLGWYQQKPGKAPKLLIYA ASSLQSGVPSRFSGSGSGTDFTLTI SSLQPEDFATYYCLQDYNYPRTFGQ GTKVEIK (SEQ ID NO. 4) |
| m-6 | EVQLVESGGGLVQPGGSLKLSCAA SGFTFSSYGMSWVRQTPDKRLELV ATINSNGGSTYYPDSVKGRFTISR DNAKNTLYLQMSSLKSEDTAMYYC ARLSYGNSFANWGQGTLVTVSS (SEQ ID NO. 5) | DIQITQSPSSLTVTAGEKVTMSCQS SQSLLNSGNHRNYLTWYQQKPGQPP KLLMYWASTRESGVPDRFAGSGSGT DFTLTISSVQAEDLAIYYCQNTYYY PFTFGSGTKLEIK (SEQ ID NO. 6) |
| m-12 | DVQLQQSGPELMKPGASVKISCKA SDYSFTSYNMHWVKQSHGKSLEW IGYIDPFNGGTRYNQKFKGKATLT VDKSSSTAYMHISSLTSEDSAVYY CARGAYYGNSFDYWGQGTLVTVS S (SEQ ID NO. 7) | DIVMTQSPSSLTVTAGEKVTMNCK SSQSLLNSGNQKNYLTWYQQKPGQ PPKLLNYWASTRESGVPDRFTGSG SGTDFTLTIGSVQAEDLAVYYCQN AYSFPFTFGSGTKLEIK (SEQ ID NO. 8) |
| m-13 | QLQLQQSGTELVRPGSSVKISCKA SGYAFSNYWMNWVKQRPGQGLEW IGQIYPGNGDTKYNGNFKGKATLT ADKSSSTAYMQLSSLTSEDSADYF CARYYRGNCFDYWGQGTTLTVSS | DIVLTQSPSSLTVTAGEKVTMSCK SSQSLLNSGNQKNYLTWYQQKPGQ PPKLLIYWASTRDSGVPARFTGSG SGTDFTLTINSVQAEDLAVYYCQN AYTYPLTFGAGTKLEIK |

TABLE 1-continued

The VH or VL sequence of the anti-CLDN18.2 monoclonal antibodies (Underlined Sequences represent CDRs, the analysis system is Kabat system)

| Clones | Heavy Chain (VH) | Light Chain (VL) |
|---|---|---|
| | (SEQ ID NO. 9) | (SEQ ID NO. 10) |
| CDRs of m-13 | GYAFSNYWMN (SEQ ID NO. 11)<br>QIYPGNGDTKYNGNFKG<br>(SEQ ID NO. 12)<br>YYRGNCFDY(SEQ ID NO. 13) | KSSQSLLNSGNQKNYLT<br>(SEQ ID NO. 14)<br>WASTRDS (SEQ ID NO. 15)<br>QNAYTYPLT (SEQ ID NO. 16) |

TABLE 2

Sequences of humanized m-13(i.e. h-13) and VH and VL thereof (Underlined Sequences represent CDRs, the analysis system is Kabat system)

| | |
|---|---|
| VH1 | QVQLVQSGAEVKKPGASVKVSCKASGYAFSNYWMNWVRQAPGQRLEWMGQIYPGNGDTKYNGNFKGRVTITRDTSASTAYMELSSLRSEDTAVYYCARYYRGNCFDYWGQGTLVTVSS(SEQ ID NO. 17) |
| VH2 | QVQLVQSGAEVKKPGASVKVSCKASGYAFSNYWMNWVRQAPGQGLEWIGQIYPGNGDTKYNGNFKGRVTITADTSASTAYMELSSLRSEDTAVYFCARYYRGNCFDYWGQGTLVTVSS(SEQ ID NO. 18) |
| VH3 | QVQLVQSGAEVKKPGASVKVSCKASGYAFSNYWMNWVKQAPGQGLEWIGQIYPGNGDTKYNGNFKGRVTITADTSASTAYMELSSLRSEDTAVYFCARYYRGNCFDYWGQGTLVTVSS(SEQ ID NO. 19) |
| VH4 | QVQLVQSGAEVKKPGASVKVSCKASGYAFSNYWMNWVKQAPGQGLEWIGQIYPGNGDTKYNGNFKGRVTLTADTSASTAYMELSSLRSEDTAVYFCARYYRGNCFDYWGQGTLVTVSS(SEQ ID NO. 20) |
| VH5 | QVQLVQSGAEVKKPGASVKVSCKASGYAFSNYWMNWVKQAPGQGLEWIGQIYPGNGDTKYNGNEKGRATLTADTSASTAYMELSSLRSEDTA VYFCARYYRGNCFDYWGQGTLVTVSS(SEQ ID NO. 21) |
| VL1 | DIVMTQSPDSLAVSLGERATINCKSSQSLLNSGNQKNYLTWYQQKPGQPPKLLIYWASTRDSGVPDRFSGSGSGTDFTLTISSLQAEDVAVYYCQNAYTYPLTFGGGTKVEIK(SEQ ID NO. 22) |
| VL2 | DIVMTQSPDSLAVSLGERATINCKSSQSLLNSGNQKNYLTWYQQKPGQPPKLLIYWASTRDSGVPDRFSGSGSGTDFTLTISSVQAEDVAVYYCQNAYTYPLTFGGGTKVEIK(SEQ ID NO. 23) |
| VL3 | DIVMTQSPDSLAVSLGERATMNCKSSQSLLNSGNQKNYLTWYQQKPGQPPKLLIYWASTRDSGVPDRFSGSGSGTDFTLTISSVQAEDVAVYYCQNAYTYPLTFGGGTKVEIK(SEQ ID NO. 24) |

TABLE 2-1

Sequences of humanized m-6(i.e. h-6) and VH and VL thereof

| Clones | Heavy Chain (VH) | Light Chain (VL) |
|---|---|---|
| h-6 | EVQLVESGGGLVQPGGSLRLSCAASGFTFSSYGMSWVRQAPGKGLEWVATINSNGGSTYYPDSVKGRFTISRDNAKNTLYLQMNSLRAEDTAVYYCARLSYGNSFANWGQGTTVTVSS (SEQ ID NO. 29) | DIVITQSPSSLSVTLGERATLSCRSSQSLLNSGNHRNYLTWYQQKPGQAPRLLMYWASTRESGVPDRFSGSGSGTDFTLTISSLQPEDFATYYCQNTYYYPFTFGGGTKLEIK (SEQ ID NO. 30) |

TABLE 3

VH and VL sequences of CD3 arm (CD3 Parental and CD3-v1, CD3-v2) (Underlined Sequences represent CDRs, the analysis system is Kabat system)

| Clones | Heavy Chain (VH) | Light Chain (VL) |
|---|---|---|
| CD3 Parental (i.e. CD3-p) | EVQLVESGGGLVQPGGSLKLSCAASGFTFNKYAMNWVRQAPGKGLEWVARIRSKYNNYATYYADSVKDRFTISRDDSKNTAYLQMNNLKTEDT | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNR |

TABLE 3-continued

VH and VL sequences of CD3 arm (CD3 Parental and CD3-v1, CD3-v2) (Underlined Sequences represent CDRs, the analysis system is Kabat system)

| Clones | Heavy Chain (VH) | Light Chain (VL) |
|---|---|---|
| | AVYYCVRHGNFGNSYISYWAYW GQGTLVTVSS (SEQ ID NO. 25) | WVFGGGTKLTVL (SEQ ID NO. 26) |
| CD3-V1 | EVQLVESGGGLVKPGGSLKLSCAA SGFTFSTYAMNWVRQAPGKGLEW VARIRSKYNNYATYYADSVKDRF TISRDDSKNTAYLQMNNLRTEDT AVYYCVRHGNWGNSYISYWAYWG QGTTVTVSS (SEQ ID NO. 27) | QTVVTQEPSLTVSPGGTVTLTCGSS TGAVTSGYYPNWVQQKPGQAPRGL IGGTKFLAPGTPARFSGSLLGGKA ALTLSGVQPEDEAEYYCALWYSNR WVFGGGTKLTVL (SEQ ID NO. 26) |
| CD3-V2 | EVQLVESGGGLVKPGGSLKLSCAA SGFTFSTYAMNWVRQAPGKGLEWV ARIRSKYNNYATTYADSVKDRFTI SRDDSKNTAYLQMNNLRTEDTAVY YCVRHGNWGNSYISYWAYWGQG TTVTVSS (SEQ ID NO. 28) | QTVVTQEPSLTVSPGGTVTLTCGSS TGAVTSGYYPNWVQQKPGQAPRGL IGGTKFLAPGTPARFSGSLLGGKA ALTLSGVQPEDEAEYYCALWYSNR WVFGGGTKLTVL (SEQ ID NO. 26) |
| CDRs of CD3 Parental | SEQ ID NO. 31: KYAMN SEQ ID NO. 32: RIRSKYNNYATYYADSVKD SEQ ID NO. 33: HGNFGNSYISYWAY | SEQ ID NO. 34: GSSTGAVTSGYYPN SEQ ID NO. 35: GTKFLAP SEQ ID NO. 36: ALWYSNRWV |
| CDRs of CD3-V1 | SEQ ID NO. 37: TYAMN SEQ ID NO. 38: RIRSKYNNYATYYADSVKD SEQ ID NO. 39: HGNWGNSYISYWAY | SEQ ID NO. 34: GSSTGAVTSGYYPN SEQ ID NO. 35: GTKFLAP SEQ ID NO. 36: ALWYSNRWV |
| CDRs of CD3-V2 | SEQ ID NO. 37: TYAMN SEQ ID NO. 40: RIRSKYNNYATTYADSVKD SEQ ID NO. 39: HGNWGNSYISYWAY | SEQ ID NO. 34: GSSTGAVTSGYYPN SEQ ID NO. 35: GTKFLAP SEQ ID NO. 36: ALWYSNRWV |

TABLE 4

Linker and constant region used in the anti-CLDN18.2 clones or CLDN18.2-13/CD3 bispecific antibodies

| DESCRIPTION | SEQUENCE | SEQ ID NO: |
|---|---|---|
| Linker-1 | GGGGSGGGGSGGGGS | 41 |
| Linker-2 | GGGGSGGGGSGGGGSGGGGSGGGGSGGGGS | 42 |
| CL (constant region of human kappa light chain) | RTVAAPSVFIFPPSDEQLKSGTASVVCLLNNFYP REAKVQWKVDNALQSGNSQESVTEQDSKDSTYSL SSTLTLSKADYEKHKVYACEVTHQGLSSPVTKSF NRGECTS | 43 |
| CH1 of human IgGI heavy chain | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKKV | 44 |
| Hinge | EPKSCDKTHTCPPCP | 45 |
| CH2 of human IgG1 heavy chain | APEAAGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALAA PIEKTISKAK | 46 |
| CH3 of human IgG1 heavy chain | GQPREPQVYTLPPSREEMTKNQVSLTCLVKGFYP SDIAVEWESNGQPENNYKTTPPVLDSDGSFFLYS KLTVDKSRWQQGNVFSCSVMHEALHNHYTQKS LSLSPGK | 47 |

TABLE 4-continued

Linker and constant region used in the anti-CLDN18.2 clones or CLDN18.2-13/CD3 bispecific antibodies

| DESCRIPTION | SEQUENCE | SEQ ID NO: |
|---|---|---|
| constant region of mouse IgG2a heavy chain | AKTTAPSVYPLAPVCGDTTGSSVTLGCLVKGYFPEPV TLTWNSGSLSSGVHTFPAVLQSDLYTLSSSVTVTSST WPSQSITCNVAHPASSTKVDKKIEPRGPTIKPCPPCK CPAPNLLGGPSVFIFPPKIKDVLMISLSPIVTCVVVD VSEDDPDVQISWFVNNVEVHTAQTQTHREDYNSTLRV VSALPIQHQDWMSGKEFKCKVNNKDLPAPIERTISKP KGSVRAPQVYVLPPPEEEMTKKQVTLTCMVTDFMPED IYVEWTNNGKTELNYKNTEPVLDSDGSYFMYSKLRVE KKNWVERNSYSCSVVHEGLHNHHTTKSFSRTPGK | 48 |
| hinge area of constant region of mouse IgG2a heavy chain | EPRGPTIKPCPPCKCP | 49 |
| CH1 of constant region of mouse IgG2a heavy chain | AKTTAPSVYPLAPVCGDTTGSSVTLGCLVKGYFPEPV TLTWNSGSLSSGVHTFPAVLQSDLYTLSSSVTVTSST WPSQSITCNVAHPASSTKVDKKI | 50 |
| CH2 + CH3 of constant region of mouse IgG2a heavy chain | APNLLGGPSVFIFPPKIKDVLMISLSPIVTCVVVDVS EDDPDVQISWFVNNVEVHTAQTQTHREDYNSTLRVVSA LPIQHQDWMSGKEFKCKVNNKDLPAPIERTISKPKGS VRAPQVYVLPPPEEEMTKKQVTLTCMVTDFMPEDIY VEWTNNGKTELNYKNTEPVLDSDGSYFMYSKLRVEK KNWVERNSYSCSVVHEGLHNHHTTKSFSRTPGK | 51 |
| CL (constant region of mouse kappa light chain) | RADAAPTVSIFPPSSEQLTSGGASVVCFLNNFYPKDI NVKWKIDGSERQNGVLNSWTDQDSKDSTYSMSSTLTL TKDEYERHNSYTCEATHKTSTSPIVKSFNRNEC | 52 |

EXAMPLES

Example 1. Anti-CLDN18.2 Monoclonal Antibodies and Confirmation of Binding Capacity and Specificity of the Anti-CLDN18.2 Monoclonal Antibodies to CLDN18.2 Protein or CLDN18.2 Expressing Cells 1. Lead Murine Anti-Human CLDN18.2 Antibodies and Humanized Anti-CLDN18.2 Antibodies We selected three lead murine anti-human CLDN18.2 antibodies (m-anti-human CLDN18.2-6 (also referred to as m-6), m-anti-human CLDN18.2-12 (also referred to as m-12), and m-anti-human CLDN18.2-13 (also referred to as m-13), and two humanized CLDN18.2 antibodies hCLDN18.2 808 and hCLDN18.2 841. VH and VL sequences thereof are listed in Table 1.

2. The Kinetics of CLDN18.2 Monoclonal Antibody m-13 Binding to hCLDN18.2 Protein were Measured Using a BIAcore 8K Instrument Based on Surface Plasmon Resonance (SRP) Technology.

VH and VL sequences of m-13 are shown in Table 1, the heavy chain constant region of m-13 is the constant region of mouse IgG2a heavy chain, and the light chain of m-13 is a mouse kappa light chain. The sequences thereof are listed in Table 4.

For kinetic measurements, hCLDN18.2 protein (Genscript) was serially diluted with HBS-EP$^{+}$1× (cytiva, BR-1006-69) buffer, starting at 50 nM, with 4 concentration gradients of 2-fold dilution and set 0 concentration. Startup 3 times. m-13 antibody: 2 μg/mL, injection time 100 s, flow rate 10 μL/min, captured with ProA chip (cytiva, 29127556); antigen protein hCLDN18.2(Genscript): binding for 120 s, flow rate 30 μL/min, dissociation for 600 s; regeneration: regeneration with $MgCl_2$ buffer for 30 s, flow rate 30 μL/min.

Figure 2A:
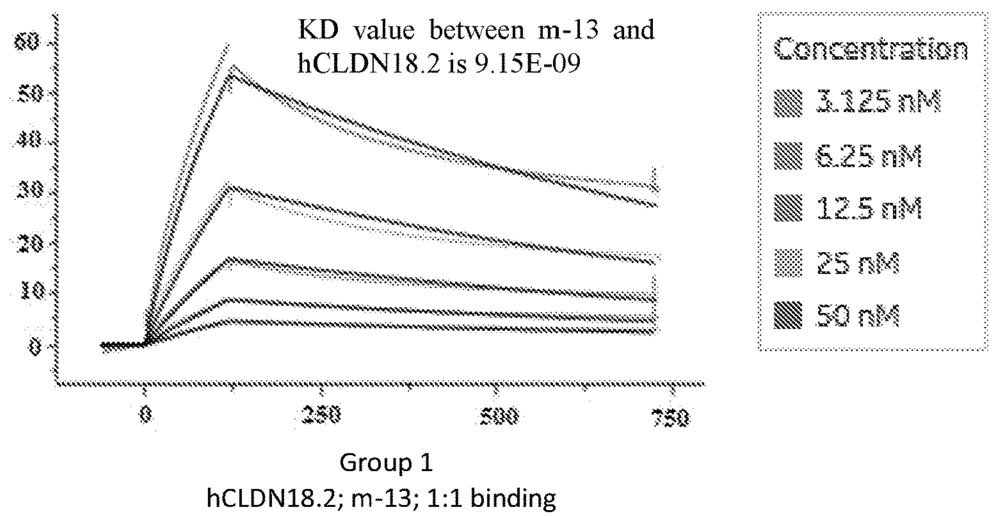
FIG. 2A-2C. Confirmation of binding affinity of CLDN18.2 monoclonal antibody m-13 to hCLDN18.2 protein (FIG. 2A), CLDN18.2 overexpressing HEK293 cells (FIG. 2B) and SNU601 cells (FIG. 2C).

The binding constant (ka) and dissociation constant (kd) were calculated using the 1:1 binding model (BIAcore Evaluation Software version 3.2), and the Equilibrium Dissociation Constant (KD) was calculated as the ratio of kd/ka. The results can be seen in FIG. 2A, and the KD value between m-13 and hCLDN18.2 is 9.15E-09.

3. Confirmation of Binding Affinity of CLDN18.2 Monoclonal Antibody m-13 to CLDN18.2 Overexpressing HEK293 Cells and SNU601 Cells 3.1 We First Compared Binding Affinity of the CLDN18.2 Monoclonal Antibodies to Human CLDN18.2-Overexpressing HEK293 Cells.

Figure 2B:
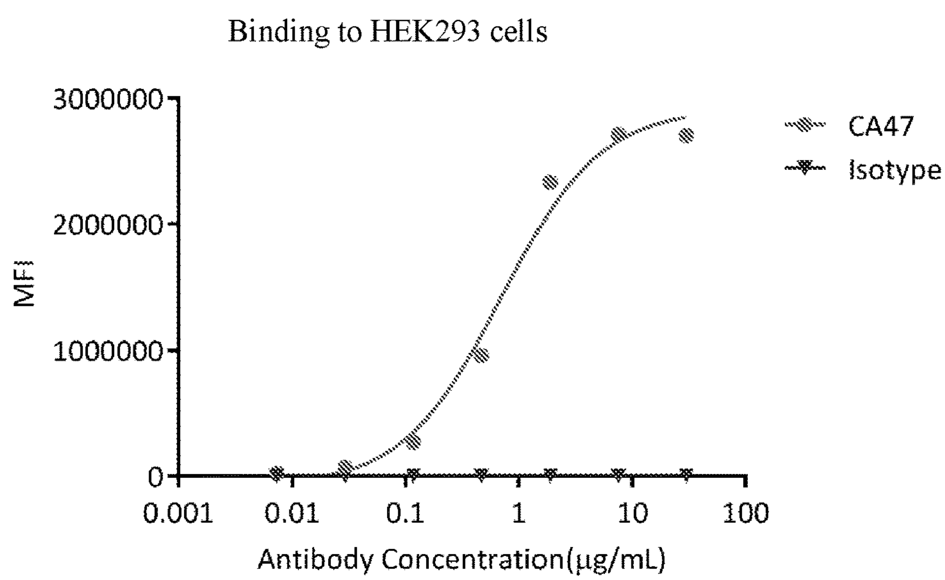

To determine binding of CLDN18.2 monoclonal antibody on the cell surface; fifty thousand hCLDN18.2-expressing HEK293 cells (KYinno) per well were placed in a 96-well V-bottom plate (Corning) and incubated with test monoclonal antibody m-13 on ice for 30 minutes. HEK293 cells were washed with FACS buffer (PBS, 2% FBS, 1 mM EDTA) and stained with goat anti-human-IgG-PE Fab (Jackson Immuno Research) on ice for 30 minutes. HEK293 cells were washed twice with FACS buffer and DAPI was added to the final suspension, and the apparent binding activity was assessed by flow cytometry and the results are shown in FIG. 2B. IC50=0.701 μg/mL, and the Isotype used in FIG. 2B is an antibody for another target but has the same Fc with m-13.

3.2 We Further Compared Binding Affinity of the CLDN18.2 Monoclonal Antibodies to Human SNU601 Cells.

Figure 2C:
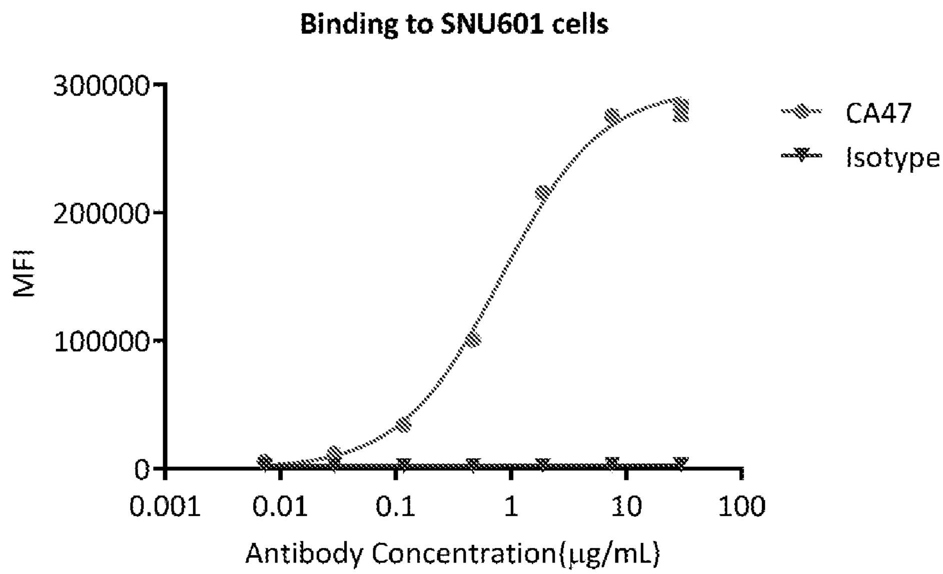

To determine binding of CLDN18.2 monoclonal antibody on the cell surface; fifty thousand SNU601 cells (Cobioer) per well were placed in a 96-well V-bottom plate (Corning) and incubated with test monoclonal antibody m-13 on ice for 30 minutes. SNU601 cells were washed with FACS buffer (PBS, 2% FBS, 1 mM EDTA) and stained with goat antihuman-IgG-PE Fab (Jackson Immuno Research) on ice for 30 minutes. SNU601 cells were washed twice with FACS buffer and DAPI was added to the final suspension, and the apparent binding activity was assessed by flow cytometry and the results are shown in FIG. 2C. IC50=0.811 μg/mL, and the Isotype used in FIG. 2C is an antibody for another target but has the same Fc with m-13.

Example 2. Generation of CLDN18.2/CD3 Bispecific Antibodies and Evaluation of the Bispecific Antibodies 1. Generation of CLDN18.2/CD3 Bispecific Antibodies and Evaluation of the Bispecific Antibodies and Lead CLDN18.2/CD3 Bispecific Antibodies Candidate Selection 1.1. Generation of CLDN18.2/CD3 Bispecific Antibodies The above two lead humanized CLDN18.2 antibodies (hCLDN18.2 808 and hCLDN18.2 841) and three lead murine anti-human CLDN18.2 antibodies (m-anti-human CLDN18.2-6 (also referred to as m-6), m-anti-human CLDN18.2-12 (also referred to as m-12), and m-anti-human CLDN18.2-13 (also referred to as m-13) were used to develop a new CLDN18.2/CD3 bispecific antibody (bispecific antibody against human CLDN18.2 and CD3) for CLDN18.2 positive tumor therapy. Humanized anti-CD3 antibody: SP34(i.e. CD3-p or CD3 Parental), CD3-v1, or CD3-v2 were used as one arm to construct CLDN18.2/CD3 bispecific antibody in a butterfly format (FIG. 1).

In this butterfly format, Fab of anti-CLDN18.2 antibody is used to bind CLDN18.2 expressed on tumor cells and two anti-CD3 scFv-arms fused to the C-terminus of the light chains of anti-CLDN18.2 is used to bind to CD3 on T cells. This format is bivalent for CLDN18.2 and functionally monovalent for CD3. Specifically, for the bispecific antibodies, anti-CLDN18.2 clone variable regions (VH and VL) were fused to the constant regions of human IgG1 heavy chain and human kappa light chain respectively; the sequences of the constant regions are listed in Table 4. The anti-CD3 single-chain variable fragment (scFv) is fused to the C terminus of the light chains of anti-CLDN18.2. To avoid Ig Fc mediated interactions, mutations L234A, L235A and P329A were introduced in the human IgG1 Fc region to eliminate effector functions (e.g. ADCC/CDC function). CLDN18.2/CD3 bispecific antibody with conventional Fc (e.g. Fc of IgG1, IgG2, IgG3 or IgG4) can also mediate killing effect.

1.2. Evaluation of Binding Affinity of the CLDN18.2/CD3 Bispecific Antibodies (i.e. CLDN18.2/CD3 bsAbs) to Human CLDN18.2-Overexpressing HEK293 Cells We first compared binding affinity of the CLDN18.2/CD3 bsAbs to human CLDN18.2-overexpressing HEK293 cells.

Figure 3A:
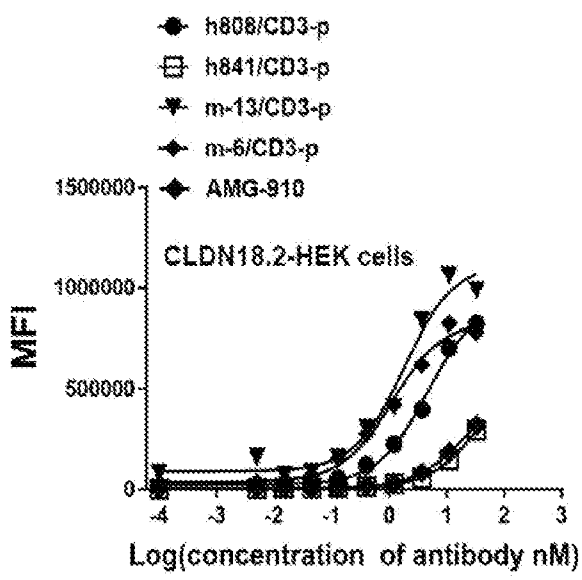
FIG. 3A-3B. Comparison of binding affinity of CLDN18.2/CD3 bispecific antibodies (h-808/CD3-p, h-841/CD3-p, m-13/CD3-p, m-6/CD3-p) with Amgen CLDN18.2/CD3 bispecific antibody(AMG-910). CLDN18.2 overexpressing HEK293 cells (FIG. 3A) and CD3 positive Jurkat cells (FIG. 3B) were stained with CLDN18.2/CD3 bispecific antibodies in serial dilution of concentrations. Mean fluorescence intensity (MFI) was determined by flow cytometry.

To determine binding of CLND18.2/CD3 bispecific antibodies on the cell surface; twenty thousand hCLND18.2-overexpressing HEK293 cells(ATCC, CRL-3216) per well were placed in a 96-well V-bottom plate (Corning) and incubated with test bsAbs (h808/CD3-p, h841/CD3-p, m-6/CD3-p, m-13/CD3-p, or AMG-910) on ice for 30 minutes. HEK293 cells were washed with FACS buffer (PBS, 2% FBS, 1 mM EDTA) and stained with goat anti-human-IgG-PE Fab (Jackson Immuno Research) on ice for 30 minutes. Cells were washed twice with FACS buffer and DAPI was added to the final suspension. The apparent binding activity was assessed by flow cytometry and the results are shown in FIG. 3A, hCLDN18.2 808/CD3 (also referred to as h-808/CD3-p) and two murine CLDN18.2/CD3-p (m-6/CD3-p and m-13/CD3-p) had comparable binding affinity to CLDN18.2, and higher binding affinity to CLDN18.2 than hCLDN18.2 841/CD3-p (also referred to h841/CD3-p) and benchmark bispecific antibody Amgen CLDN18.2/CD3 (AMG-910) (the amino acid sequence depicted in SEQ ID NO: 132 of US20200055932A1).

Figure 3B:
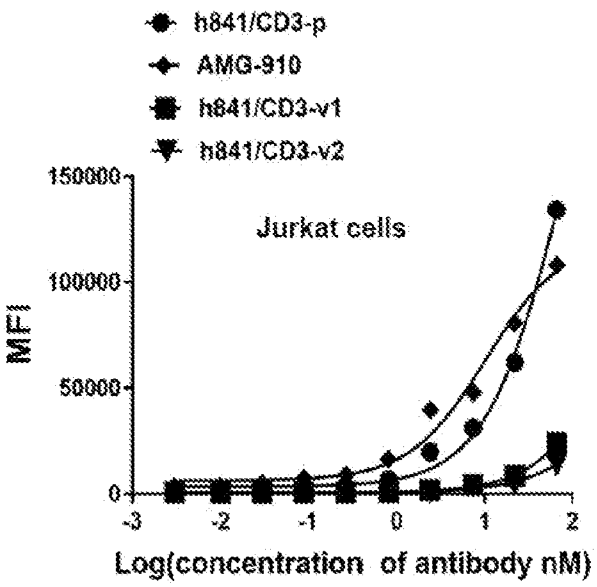

1.3. Evaluation of Binding Affinity of the CLDN18.2/CD3 Bispecific Antibodies to $CD3^+$ Jurkat Cells To compare CD3 binding affinity of Amgen CLDN18.2/CD3(AMG-910) bsAb with CLDN18.2/CD3 bsAbs having mutant anti-CD3 arm (h841/CD3-v1 and h841/CD3-v2) or having parental anti-CD3 arm (h841/CD3-p), $CD3^+$ Jurkat cells(ATCC, Clone E6-1) were stained with h841/CD3-p, h841/CD3-v1 as well as h841/CD3-v2 with both CD3-v1 and CD3-v2 having reduced CD3 binding affinity. As shown in FIG. 3B, AMG-910 bsAb showed a similar binding affinity to CD3 as h841/CD3-p bsAb having parental anti-CD3 arm (also referred to as CD3-p), but much higher binding affinity than our h841/CD3-v1 and h841/CD3-v2 having mutant anti-CD3 arm (i.e. CD3-v1 and CD3-v2) (FIG. 3B) (VH and VL sequences of CD3-p, CD3-v1 and CD3-v2 are listed in Table 3).

Figure 4:
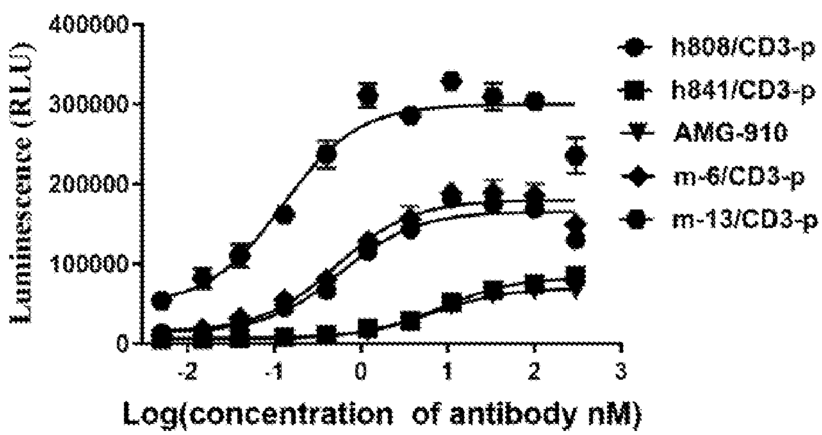
FIG. 4. TCR-NFAT activity mediated by CLDN18.2/CD3 bispecific antibodies in NFAT-reporter Jurkat cells. NFAT reporter Jurkat cells were cocultured with CLDN18.2-expressing SNU620 cells (E/T: 3/1) in serial dilutions of CLDN18.2/CD3 bispecific antibodies for 6 hours. NFAT activity was determined by relative luminescence units (RLU).

1.4. Evaluation of TCR-NFAT Activity Mediated by CLDN18.2/CD3 bsAb in NFAT-Reporter Jurkat Cells We further verified TCR-NFAT activity mediated by CLDN18.2/CD3 bsAb in NFAT-reporter Jurkat cells (InvivoGen, jktl-nfat). NFAT activity mediated by AMG-910 bsAb and h841/CD3-p was significantly lower than NFAT activity mediated by h808/CD3-p, m-6/CD3-p, and m-13/CD3-p (FIG. 4), even though h808/CD3-p, h841/CD3-p and AMG-910 had similar binding affinity to CD3. This finding indicated that TCR signaling strength triggered by CLDN18.2/CD3 bsAbs depends on binding affinity of CLDN18.2/CD3 bsAb to CD3 as well as the target molecule CLDN18.2.

1.5. Evaluation of T Cells Killing Effect Mediated by CLDN18.2/CD3 bsAb in Three Tumor Cell Lines with Various Expression Levels of hCLDN18.2

In selecting a lead candidate antibody, one of the most important functions is whether it can efficiently mediate T cells to kill targets. To evaluate this, we chose three tumor cell lines with various expression levels of hCLDN18.2 as targets. Freshly isolated human PBMCs (STEMCELL Technologies) were cocultured with the target cells in serial dilution of the tested CLDN18.2/CD3 bsAbs at E/T ratio of 20:1 for 48 hours. Killing activity to the target cells was determined by luminescence units as these target cells were transfected with luciferase. As shown in FIG. 5A-5C, three murine CLDN18.2/CD3 bsAbs (i.e. mCLDN18.2/CD3 bsAbs): m-6/CD3-p, m-12/CD3-p, and m-13/CD3-p displayed better killing activity against high CLDN18.2 expressing HEK (ATCC, CRL-3216) (i.e. $CLDN18.2^+$HEK) (FIG. 5A), medium CLDN18.2 expressing SNU620 (Korean Cell Line Bank, 00620.1) (FIG. 5B), and low CLDN18.2 expressing KATO III (ATCC, HTB-103) (FIG. 5C) target cells as compared to h841/CD3-p and AMG-910 BsAb. The differences in killing potency between mCLDN18.2/CD3 bsAbs and AMG-910 were even larger against the medium (SNU620) (FIG. 5B) and low (KATO III) expressing CLDN18.2 cells (FIG. 5C), which suggests that mCLDN18.2/CD3 bsAbs have significant potential development value with a better therapeutic index than AMG-910. FIG. 5D-5F shows EC50 of killing potency for murine CLDN18.2/CD3 bispecific antibodies.

1.6. Evaluation of Cytokines Release Mediated by CLDN18.2/CD3 bsAb

Figure 6:
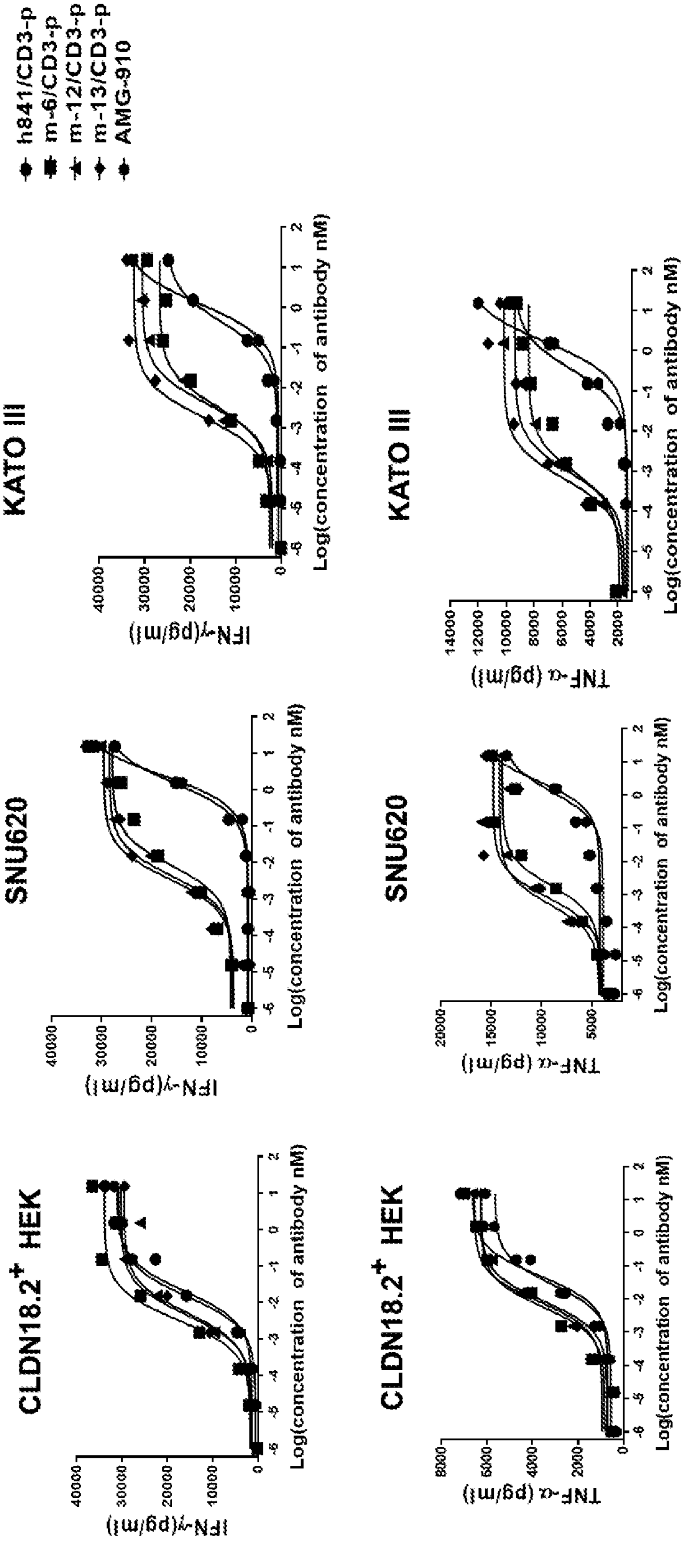
FIG. 6. Comparison of cytokine release levels mediated by murine CLDN18.2/CD3 bispecific antibodies. Freshly isolated PMBCs were isolated from healthy donors and cocultured with CLDN18.2-expressing HEK (i.e. CLDN18.2$^+$HEK), SNU620, and KATO III target cells in serial dilution of CLDN18.2/CD3 bispecific antibodies. The supernatants were collected at 48 hours. IFN-γ and TNF-α were determined by ELISA assays.

T-cell engager antibody can mediate direct cell-cell contacts between CTLs and target cells, which results in killing target cells. On the other hand, activated T cells can simultaneously secrete cytokines, such as IFN-α and TNF-γ as long as TCR stimulation continues by antibody engagement. These cytokines affect the target cell or cell distal to the effector T cells. TNF-α engages its receptor on the target cell and triggers target-cell apoptosis, and IFN-γ increases Fas-mediated target-cell lysis. However, although cytokines are necessary for the functioning of T cells, high cytokine release levels mediated by T cell engager antibody would induce a potential unfavorable cytokine release syndrome (CRS). Therefore, proper levels of cytokine release mediated by CLDN18.2/CD3 bispecific antibodies would need to be taken into consideration for evaluation of a lead candidate. For this reason, a parallel study was designed to investigate cytokine release in the same co-culture condition as the killing assay. The target cells and human PBMCs were plated in 96-well microplates at an E:T ratio of 20:1 and co-cultured with various concentrations of anti-CLDN18.2/CD3 bsAbs(h841/CD3-p, AMG-910, m-6/CD3-p, m-12/CD3-p, and m-13/CD3-p). After 48 hours of incubation, cell-free supernatants were harvested, and the production of INF-α, TNF-γ, IL-2, and IL-10 secretion was measured by ELISA in the supernatants from the coculture of PBMCs with various CLDN18.2 expressing HEK (i.e. CLDN18.2 HEK), SNU620, and KATO III target cells. In line with cytolytic activity, m-6/CD3-p, m-12/CD3-p, and m-13/CD3-p clones induced higher INF-α (FIG. 6), TNF-γ (FIG. 6), IL-2, and IL-10 release (data not shown). By contrast, lower levels of cytokine release were observed from h841/CD3-p and AMG-910.

1.7. Evaluation of Binding Specificity of Anti-CLDN18.2 Antibodies and Lead CLDN18.2/CD3 Bispecific Antibodies Candidate Selection As CLDN18.1 and CLDN18.2 share highly homologous sequences, the assessment of binding specificity of anti-CLDN18.2 antibodies is critical for the development of therapeutic Claudin18.2 bispecific antibodies. From the killing assays (FIG. 5A-5C), we found that the three murine anti-human CLDN18.2 (m-6, m-12, and m-13) CD3 bsAbs displayed more potent cytotoxicity than h841/CD3 against various CLDN18.2 expressing targets. Therefore, binding specificity of those CLDN18.2 antibodies needed to be assessed against CLDN18.1 expressing cell lines.

As described above, we tested the specificity of h808/CD-3-p, h841/CD3-p, and three murine CLDN18.2/CD3-p BsAbs on human CLDN18.1-overexpressing CHO cells (Creative Biogene, SCS-R00629). In general, after dissociating cells and washing in PBS, $1\times10^5$ CLDN18.1 expressing CHO cells were seeded in a 96 well plate. The anti-CLDN18.2/CD3 antibodies prepared in a final concentration of 25 μg/mL were incubated with cells for 1 hour at 4° C. After washing with FACS wash buffer, plates were incubated with PE conjugated goat anti-Human IgG, Fc Fragment Specific antibody (1:200 diluted in FACS wash buffer) for 20 minutes at 4° C. Mean fluorescence intensity (MFI) was measured using NovoCyte 2060 and results were analyzed by GraphPad software.

Figure 7:
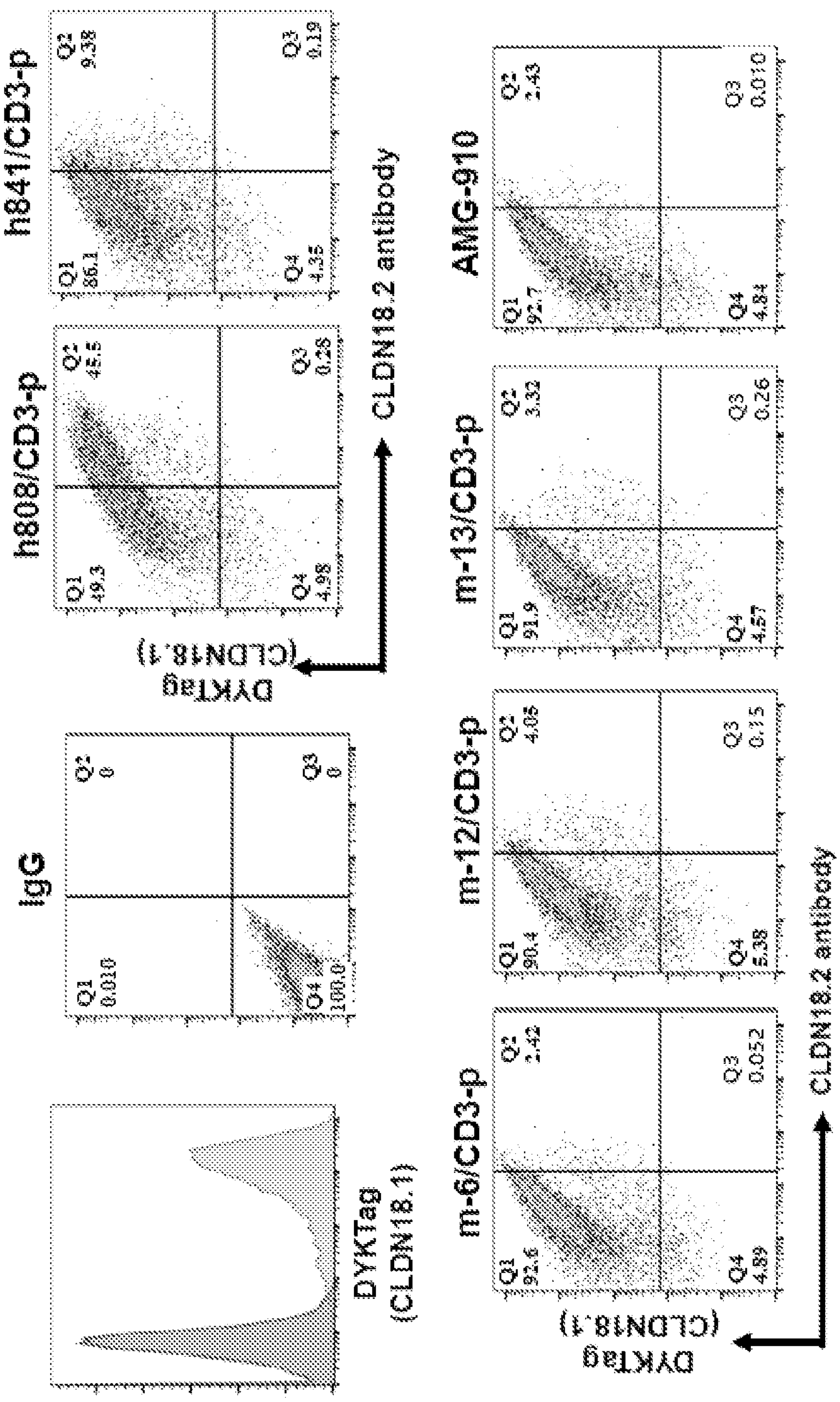
FIG. 7. Like Amgen CLDN18.2 antibodies (i.e. AMG-910), the murine CLDN18.2 antibodies (i.e. m-6/CD3-p, m-12/CD3-p, m-13/CD3-p) and h841/CD3-p antibody showed no cross-reactivity with CLDN18.1. CLDN18.1-overexpressing CHO cells were stained with h808/CD3, h841/CD3, three murine CLDN18.2/CD3 or Amgen CLDN18.2/CD3 bispecific antibodies. The top panel shows staining CLDN18.1-DYK Tag expressing CHO with DYKDDDK Epitope Tag antibody, anti-human IgG control, h808/CD3, and h841/CD3 bispecific antibodies. The bottom panel shows staining CLDN18.1-DYK tag expressing CHO cells with m-6, m-12, m-13, and Amgen CLDN18.2/CD3 bispecific antibodies.
Figure 8:
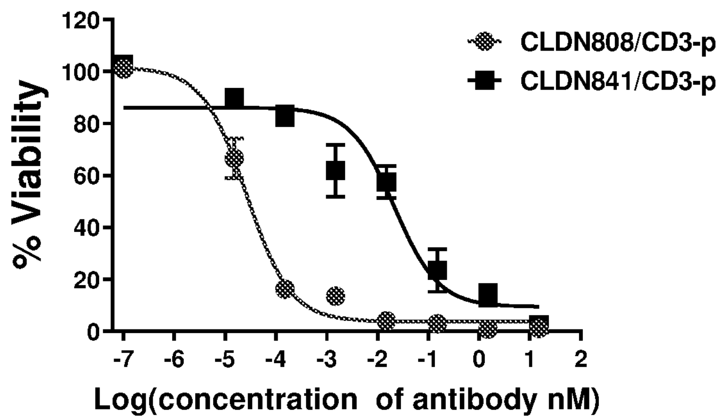
FIG. 8. Freshly isolated T cells (Effector) were cocultured with CLDN18.2 expressing SNU620 Luc target cells (T) at E/T ratio:20/1 in a serial dilution of CLDN18.2/CD3 bispecific antibodies (CLDN18.2-808/CD3 and CLDN18.2-841/CD3 bispecific antibodies) for 48 hours. Luciferase quantitative assays were performed to determine cytotoxic activity against target cells.

As shown in FIG. 7, m-6/CD3-p, m-12/CD3-p, m-13/CD3-p, h841/CD3-p and AMG-910, exhibit clear binding specificity and no cross-reactivity with human CLDN18.1-overexpressing CHO. Unexpectedly, the data from flow cytometry assays showed h808/CD3-p had high cross-reactivity with CLDN18.1. As a result, this cross-reactivity led to a devaluation of h808/CD3-p bispecific antibody as a lead candidate for further development even though it displayed very potent cytotoxicity (FIG. 8). In addition, h841/CD3-p did not show binding to CLDN18.1; however, lower binding affinity and poor killing potency to target cells were disadvantages of utilizing h841/CD3-p (FIG. 8).

Figure 9:
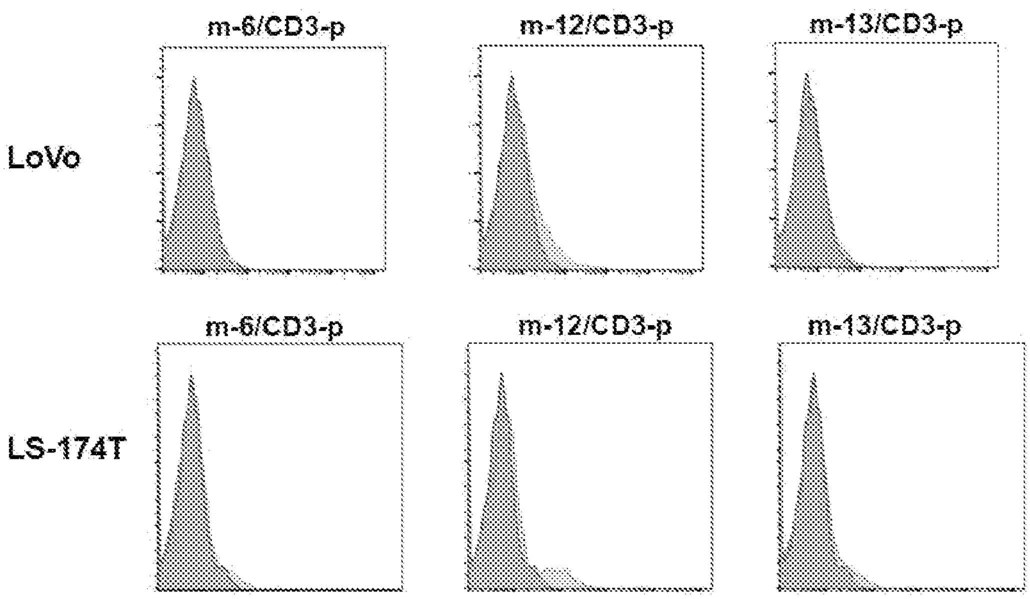
FIG. 9. Murine CLDN18.2-12 clone nonspecifically binds to CLDN18.2 negative LoVo and LS-174T cells. CLDN18.2 negative LoVo tumor cells (the top panel) and CLDN18.2 negative LS-174T tumor cells (the bottom panel) were stained with m-6, m-12, and m-13/CD3 bispecific antibodies.

To further confirm binding specificity of the murine CLDN18.2 clones m-6/CD3-p, m-12/CD3-p, m-13/CD3-p were tested against CLDN18.2 negative tumor cell lines LoVo (ACTT, CCL-229) and LS-174T (ATCC, LC-188) using flow cytometry assays. As shown in FIG. 9, m-6/CD3-p and m-13/CD3-p were not found to bind to the tested CLDN18.2 negative tumor cells, while m-12/CD3-p showed weak and non-specific binding to LoVo and LS-174T cells (FIG. 9).

Figure 10:
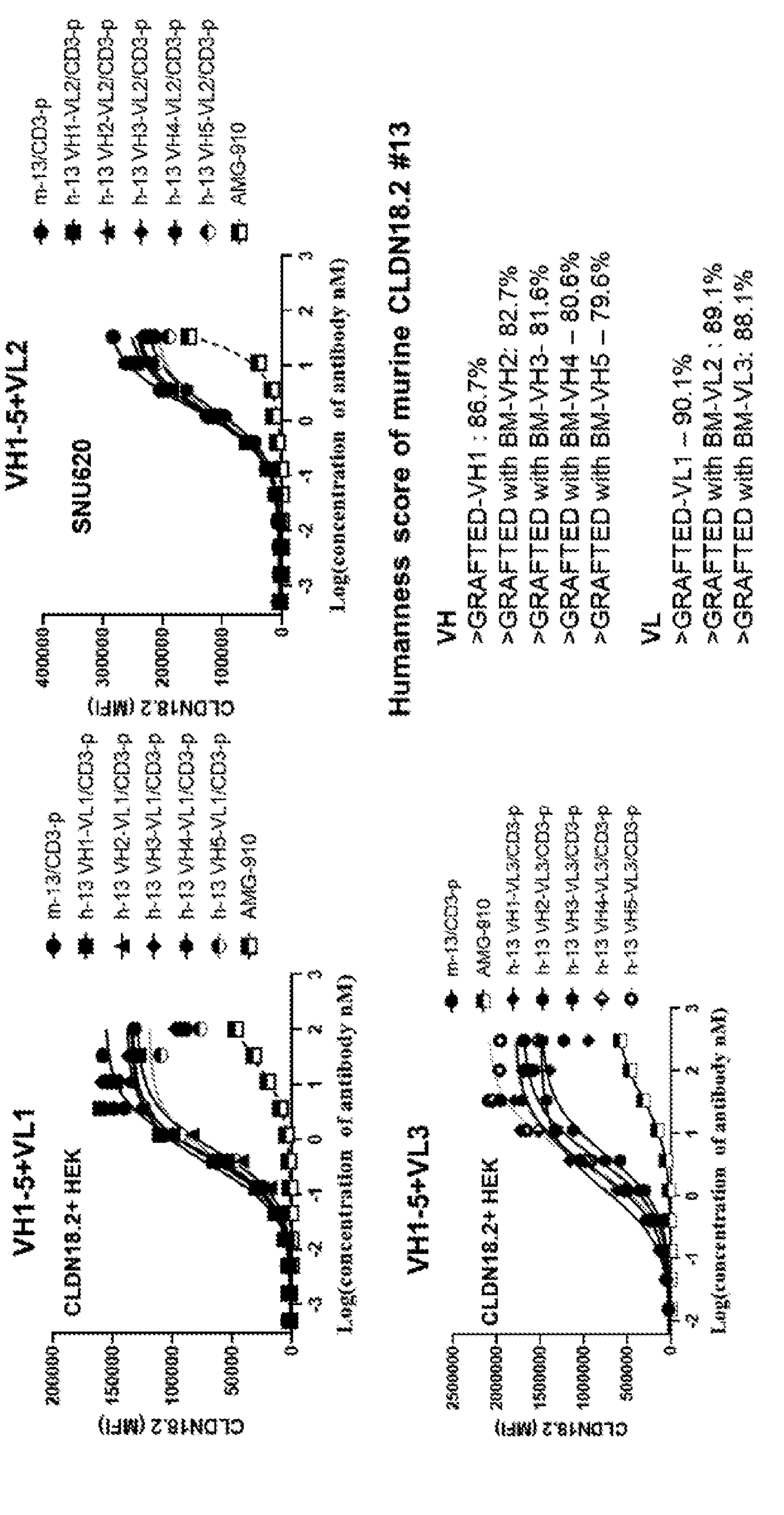
FIG. 10. Humanized CLDN18.2-13 subclones show similar binding affinity to CLDN18.2 on the cell surface. CLDN18.2-13 subclones VH1-5+VL1, parental m-13 and Amgen CLDN18.2/CD3 bispecific antibodies were used to stain CLDN18.2 overexpressing HEK cells (the top left panel); h-13 subclones VH1-5+VL2, parental m-13 and Amgen CLDN18.2/CD3 bispecific antibodies were used to stain CLDN18.2 natural expressing SNU620 cells (the top right panel); h-13 subclones VH1-5+VL3, m-13 parental and Amgen CLDN18.2/CD3 bispecific antibodies were used to stain CLDN18.2 overexpressing HEK cells (the left of the bottom panel); Humanness score of murine CLDN18.2-13 was shown in the bottom right panel.

2. Evaluation of Humanized CLDN18.2-13/CD3 Bispecific Antibodies 2.1 Binding Affinity of CLDN18.2-13/CD3 Bispecific Antibodies As m-13 and m-6 clones displayed high binding affinity, high specificity, and potent cytotoxicity, m-13 was finally chosen as a lead candidate for humanization and m-6 also was humanized as a back-up clone. The VH and VL sequences of humanized m-6 (i.e., h-6) are shown as SEQ ID Nos. 29-30 listed in Table 2-1, respectively. For m-13, the top 3 humanized variable light chains and 5 variable heavy chains were obtained, which reached high human-ness scores (VL1-90.1%, VL2-89.1%, VL3-88.1%, VH1-86.7%, VH2-82.7%, VH3-81.6%, VH4-80.6%, and VH5-79.6%) (VH and VL sequences are listed in Table 2). To characterize the CLDN18.2-13 antibodies (i.e. CLDN18.2-h-13 antibodies) resulting from those humanized heavy chains (i.e. VH1-VH5) and light chains (i.e. VL1-VL3), each humanized light chain was co-transfected with each humanized CLDN18.2-13 heavy chain in CD3 bispecific format. As a result, 15 humanized CLDN18.2-13/CD3 bispecific antibodies were generated. To determine their apparent binding activity, high CLDN18.2 expressing HEK293 and SNU620 cell lines as targets were incubated in varying concentrations of humanized CLDN18.2/CD3 bispecific antibodies, and with anti-human IgG-PE as a secondary antibody. The cells were then washed twice with FACS buffer. FACS analysis was carried out on a FACS Flow Cytometer. Through flow cytometry assays, we characterized the binding affinity of humanized CLDN18.2-13/CD3 subclones to CLDN18.2 on hCLDN18.2 over-expressing HEK293 cells (high expression of CLDN18.2) and CLDN18.2 natural expressing SNU-620 cells (medium expression of CLDN18.2). We found that all 15 humanized CLDN18.2-13/CD3 candidates had comparable binding affinities as parental m-13 (FIG. 10) as judged by median fluorescence intensity (MFI) on both CLDN18.2 highly expressing HEK cells as well as CLDN18.2 medium expressing SNU620 cells.

2.2 High Specificity of CLDN18.2-13/CD3 Bispecific Antibodies

Figure 11:
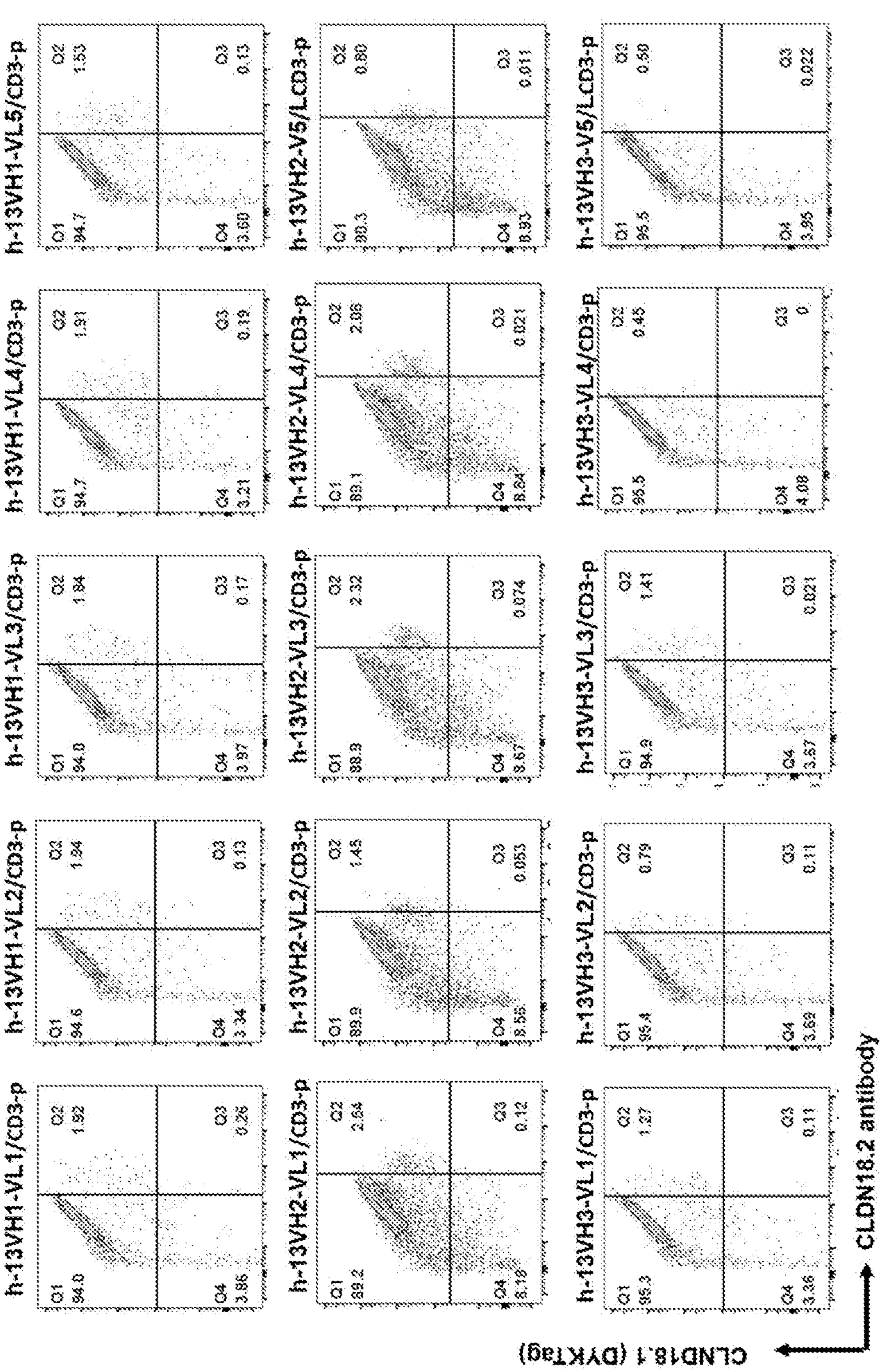
FIG. 11. High specificity of CLDN18.2-13/CD3 bispecific antibodies. CLDN18.1-overexpressing CHO cells were stained with h-13 VH1-5+VL1 (the top panel), VH1-5+VL2 (the middle panel), and LV3+HV1-5 (the bottom panel) subclone/CD3 bispecific antibodies.

Although all humanized CLDN18.2-13/CD3 bsAbs retained high binding affinity to CLDN18.2 similar to parental m-13, whether the humanization of m-13 clone would change binding specificity was also very important to determine for the resultant humanized heavy chains and light chains. Therefore, we examined binding specificity of humanized CLDN18.2-13/CD3 subclones by staining human CLDN18.1 overexpressing CHO cells. As shown in FIG. 11, all 15 humanized CLDN18.2-13 subclones had no binding to CLDN18.1 on the transfected CHO cells, which suggests that humanized CLDN18.2 heavy and light chains retained binding specificity to CLDN18.2 similar to their parental m-13.

2.3 TCR/CD3 Signaling Strength Mediated by CLDN18.2-13/CD3 Bispecific Antibodies (i.e. h-13/CD3 bsAbs) with CD3-p (i.e. CD3 Parental) Arm.

In addition to binding affinity, TCR/CD3 signaling strength mediated by humanized CLDN18.2-13/CD3 subclones was also validated using coculture of NFAT-luciferase Jurkat cells with CLDN18.2$^+$ SNU620 cells for 6 hours. To do so, $1\times10^5$ Jurkat NFAT-luciferase reporter cells and $1\times10^5$ CLDN18.2-expressing NSU620 tumor cells were seeded in a 96-well plate and incubated in 100 μL media+ 10% FBS and a serial dilution of anti-CEA/CD3 bsAbs at 37° C. for 6 hours. Bio-Glo™ Reagent (Promega) was added and luminescence was quantified using the BioMax Discover system. The data were fitted to a 4PL curve using GraphPad Prism 8 software.

Figure 12:
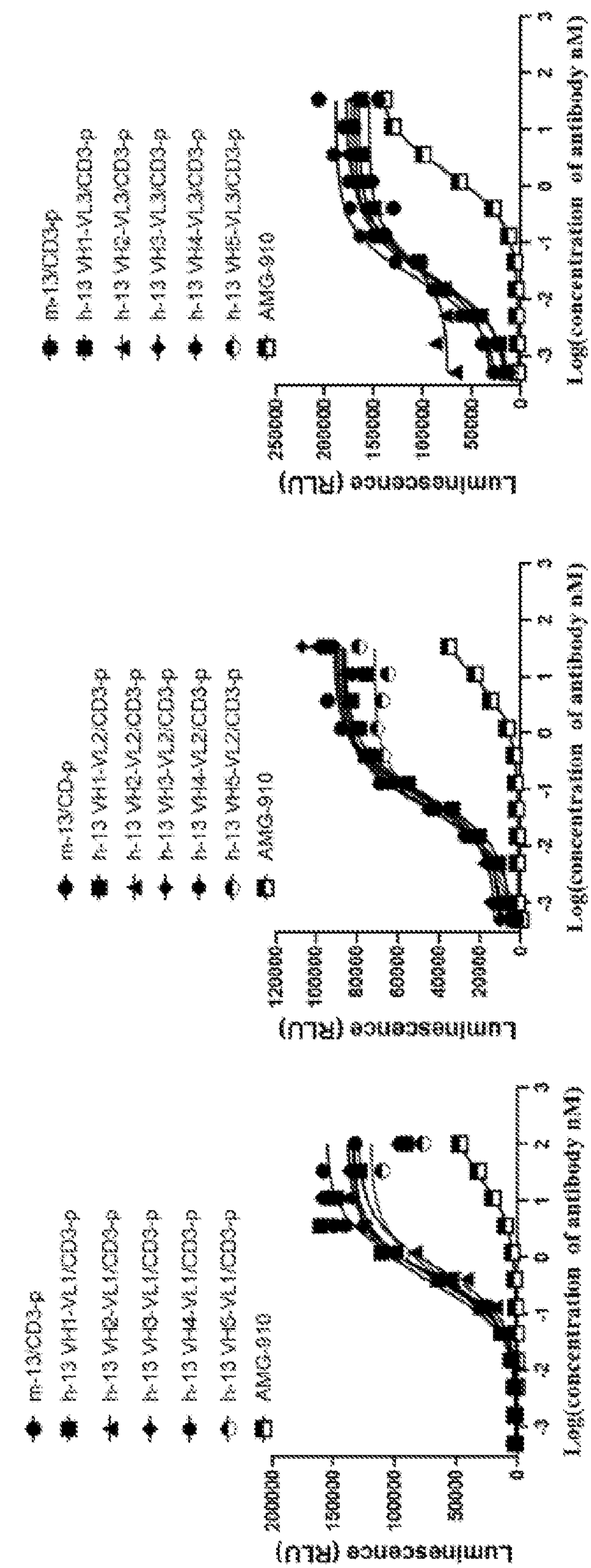
FIG. 12. Comparable NFAT activity mediated by humanized CLDN18.2-13/CD3-p bispecific antibodies as the parental murine CLDN18.2-13/CD3-p. NFAT reporter Jurkat cells were cocultured with CLDN18.2 expressing SNU620 cells (E/T: 3/1) in serial dilutions with hCLDN18.2-13 VL1+VH1-5 (the left panel), VL2+VH1-5 (the middle panel), and VL3+VH1-5 (the right panel) subclone/CD3 bispecific antibodies for 6 hours. NFAT activity was determined by relative luminescence units (RLU).

NFAT activity mediated by the 15 humanized CLDN18.2-13/CD3-p subclones, m-13/CD3-p, and Amgen CLDN18.2/CD3 bsAbs (AMG-910) were compared based on the luminescence readout. As expected, humanized CLDN18.2-13/CD3-p subclones induced a similar level of NFAT activity as their parental m-13/CD3-p (FIG. 12).

2.4 Anti-Tumor Effect of CLDN18.2-13/CD3 Bispecific Antibodies (i.e. h-13/CD3 bsAbs) with CD3-p (i.e. CD3 Parental) Arm Finally, we compared the anti-tumor effect of humanized CLDN18.2-13/CD3 subclones (i.e.h-13/CD3-p subclones) with m-13/CD3-p. CLDN18.2 over-expressing HEK/Luc cells (i.e. CLDN18.2$^+$HEK) (ATCC, CRL-3216) and medium CLDN18.2 expressing SNU620 cells were cocultured with PBMCs in serial dilutions of the tested antibodies at a final E/T ratio of 20:1. Specific lysis of tumor cells was determined after a 48-hour coculture by quantification of luciferase intensity units. As shown in FIG. 13, the humanized CLDN18.2-13/CD3 subclones induced potent T cell redirected cytotoxicity against their targets. As expected, the killing potency mediated by humanized CLDN18.2-13/CD3 subclones and parental m-13/CD3-p was 100-fold higher than that of AMG-910 (FIG. 13). Taken together, these functional assays indicated that the murine CLDN18.2 clone 13 has been successfully humanized.

2.5 Binding Affinity of CLDN18.2-13/CD3 Bispecific Antibodies (i.e. h-13/CD3 bsAbs) with Mutant CD3 Arm (CD3-V1 or CD3-V2) to CLDN18.2 and CD3

Since h-13/CD3-p carried SP34 as a CD3 arm, which has high binding affinity to CD3, potential cytokine release syndrome (CRS) may be induced in the clinic. To generate safe and effective CLDN18.2/CD3 bispecific antibody and to reduce the potential CRS related toxicity, we used our optimized CD3 platform, which includes several CD3 binders with various binding affinities. Our previous project has already demonstrated that the usage of the lower binding CD3 binders as arms for construction of CEA/CD3 bispecific antibodies can significantly reduce cytokine release and still retain a potent killing activity.

Therefore, the humanized CLDN18.2-13 heavy chain 1 (VH1) was used to co-transfect CHO cells with h-13 light chains (VL1) linked with the CD3-P, or mutant CD3 binders (CD3-V1 and CD3-V2) (sequences are listed in Table 3). Eventually, three h-13/CD3 variant bispecific antibodies were generated, h-13VH1-VL1/CD3-p, h-13VH1-VL1/CD3-v1, and h-13VH1-VL1/CD3-v2. As the mutant CD3 scFv was linked to hCLDN18.2 light chain, we first examined whether binding affinity of h-13/CD3-v1 and h-13/CD3-v2 to CLDN18.2 on the cell surface would be affected. Therefore, CLDN18.2 positive SNU620 cells were stained with h-13/CD3 variant bispecific antibodies by FACS assay. As shown in FIG. 14A, all h-13/CD3 subclones had comparable binding affinity to CLDN18.2 as their parental m-13 binders (i.e.m-13/CD3-p). FIG. 14B shows EC50 of binding affinity of humanized CLDN18.2/CD3 bispecific antibodies compared with murine parental CLDN18.2-13/CD3 bispecific antibody.

To confirm binding of CD3 variants to CD3 on T cells, we performed a Jurkat binding assay. As we expected, FACS analysis showed that h-13/CD3-v1 and h-13/CD3-v2 displayed significantly reduced binding affinities compared to h-13/CD3-p with parental CD3 binders (i.e.m-13/CD3-p) (FIG. 14C). FIG. 14D shows EC50 of binding affinity of humanized CLDN18.2/CD3 bispecific antibodies compared with murine parental CLDN18.2-13/CD3 bispecific antibody.

2.6 TCR Signaling Mediated by of CLDN18.2-13/CD3 Bispecific Antibodies (i.e. h-13/CD3 bsAbs) with Mutant CD3 Arm (CD3-V1 or CD3-V2)

We then further evaluated the strength of TCR signaling mediated by h-13/CD3 bsAbs by NFAT reporter assay. As described in section 2.3, Jurkat NFAT-luciferase reporter cells and CLDN18.2-expressing NSU620 tumor cells were seeded in a 96-well plate and incubated for 6 hours. Luminescence was quantified using the BioMax Discover system.

Consistent with their binding affinity (FIG. 14C), three h-13/CD3-v2 subclones and the h-13/CD3-v1 subclone induced lower NFAT activity as compared to h-13/CD3-p in coculture of Jurkat-NFAT reporter cells with SNU620 target cells (FIG. 15). However, there is still higher NFAT activity mediated by h-13/CD3-v1 and h-13/CD3-v2 subclones than that of Amgen 18.2/CD3 bsAb (i.e. AMG-910) that carried a higher CD3 binding affinity binding arm, which once again suggested that binding affinity to CLDN18.2 also plays an important role in the T cell engagers.

2.7 Cytolytic Potency Mediated by CLDN18.2-13/CD3 Bispecific Antibodies (i.e. h-13/CD3 bsAbs) with Mutant CD3 Arm (CD3-V1 or CD3-V2)

Figure 16:
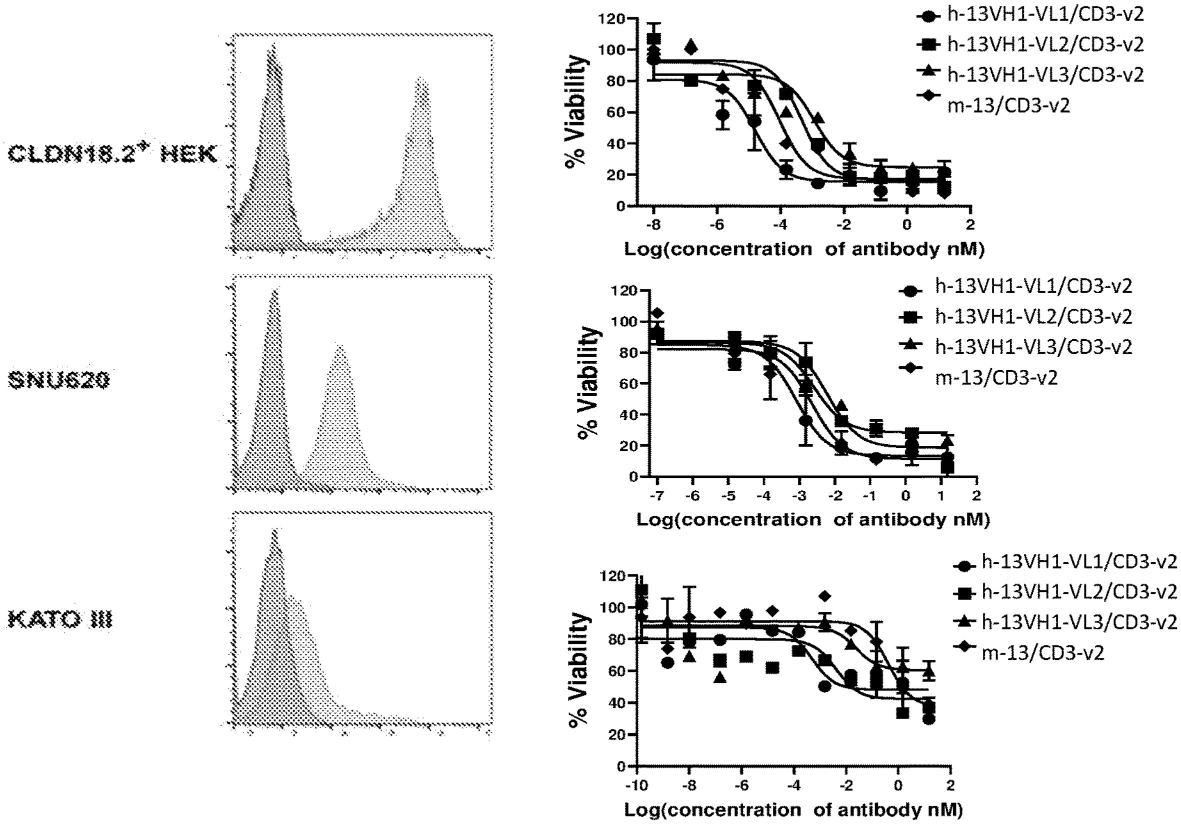
FIG. 16. Comparison of killing potency mediated by h-13/CD3 bispecific antibodies against various CLDN18.2-expressing targets. CLDN18.2-overexpressing HEK (i.e. CLDN18.2 HEK), CLDN18.2 naturally expressing SNU620 and CLDN18.2 naturally expressing KATO III target cells were harvested, counted and seeded in 96-well plates. Effector PBMCs were added to each well in a proportion of 20:1 in RPMI 1640. Serial dilutions of the indicated antibodies were performed in RPMI 1640 medium and added to the target/effector-containing well. The plates were incubated for 48 hours, and Luciferase intensity was determined.

As CLDN18.2-13/CD3-v2 has lower binding affinity to CD3, which will significantly reduce cytokine release, three CLDN18.2/CD3-v2 bispecific antibodies with VH1 plus different VL1-3 chains were generated. As a result, we further compared cytolytic potency mediated by the 3 h-13/CD3 subclones using various CLDN18.2-expressing HEK (i.e. CLDN18.2$^+$HEK), SNU620 and KATO III cells as a tumor target (FIG. 16 left panel). Interestingly, h-13VH1-VL1/CD3-v2 showed the highest potency against various CLDN18.2 expressing targets among the m-13/CD3-v2 clone and humanized h-13/CD3-v2 subclones (FIG. 16 right panel) in spite of similar binding and NFAT activity as the other h-13/CD3-v2 subclones (FIG. 15).

2.8 Cytokine Release Level Mediated by CLDN18.2-13/CD3 Bispecific Antibodies (i.e. h-13/CD3 bsAbs) with Mutant CD3 Arm (CD3-V1 or CD3-V2)

Moreover, since cytokine release level is usually correlated with killing potency, we further compared the cytokine release from the supernatants of SNU620 and PBMCs coculture system.

Figure 17:
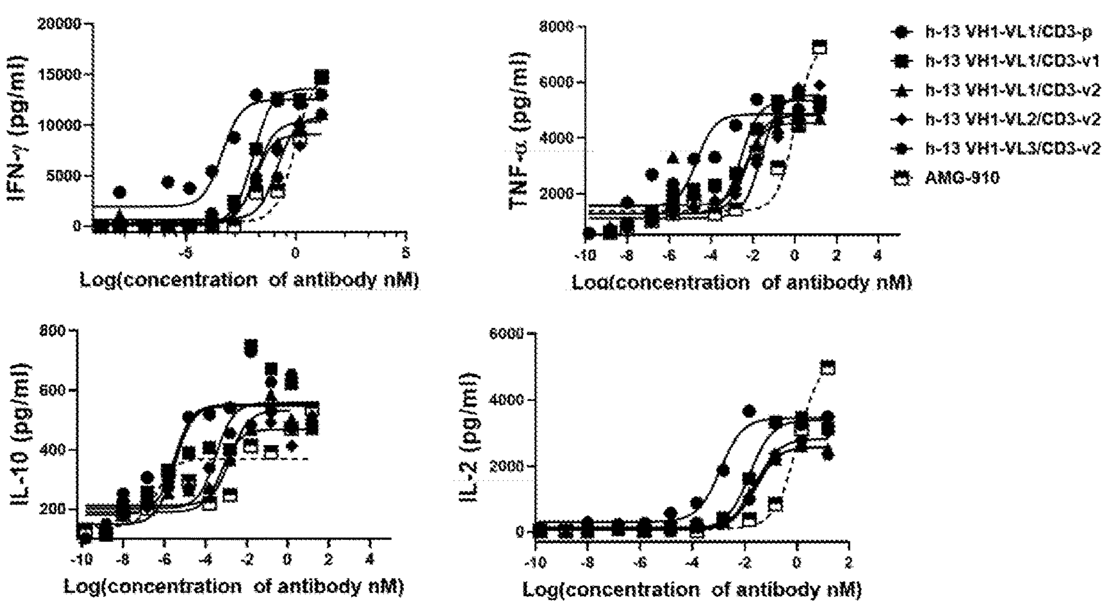
FIG. 17. Comparison of cytokine release mediated by CLDN18.2-13/CD3 bispecific antibodies. Freshly isolated PBMCs were isolated from healthy donors and cocultured with CLDN18.2-expressing SNU620 target cells in serial dilutions of the indicated CLDN18.2/CD3 bispecific antibodies with various binding affinities of CD3. The supernatants were collected at 48 hours. IFN-γ, TNF-α, IL-2, and IL-10 concentrations were determined by ELISA assays.

As described in Section 1.6, the supernatants of SNU620 and PBMC coculture experiments were collected for cytokine release measurement after 48 hours. IFN-γ, TNF-α, IL-10, and IL-2 release were quantified using BD optEIA human IFNγ and TNFα ELISA kits. Briefly, ELISA plates were coated with capture antibodies overnight. The supernatants were diluted at 1:20 with ELISA buffer and detector antibodies were added after 2 hour-incubation. ELISA substrate was added and the plates were read at 450 nM in SpectraMax reader after HRP was added into each well. Interestingly, h-13VH1-VL1/CD3-v2 induced comparable IFN-γ, TNF-α, IL-10, and IL-2 release as the other two h-13/CD3-v2 subclones (FIG. 17). Most importantly, h-13/CD3-v2 subclones mediated significantly lower cytokine release as compared to h-13/CD3-p, which was clearly driven by the higher CD3 binding affinity of h-13/CD3-p. Taken together, h-13VH1-VL1/CD3-v2 was selected as the lead candidate antibody based on its higher killing potency and similar cytokine release as compared to the other two h-13/CD3-v2 subclones.

---

The invention claimed is:

1. An anti-CLDN18.2 antibody or antigen binding fragment thereof, comprising a heavy chain variable region and a light chain variable region, wherein the heavy chain variable region comprises HCDR1 comprising the amino acid sequence of SEQ ID NO. 11, HCDR2 comprising the amino acid sequence of SEQ ID NO. 12 and HCDR3 comprising the amino acid sequence of SEQ ID NO. 13, and the light chain variable region comprises LCDR1 comprising the amino acid sequence of SEQ ID NO. 14, LCDR2 comprising the amino acid sequence of SEQ ID NO. 15 and LCDR3 comprising the amino acid sequence of SEQ ID NO. 16.

2. The anti-CLDN18.2 antibody or antigen binding fragment of claim 1, wherein the antigen binding fragment is selected from scFv fragment, Fv fragment, F(ab')2 fragment, Fab' —SH fragment and Fab' fragment.

3. The anti-CLDN18.2 antibody or antigen binding fragment thereof of claim 1, wherein the antibody is a monoclonal antibody and/or the antibody is a humanized antibody.

4. The anti-CLDN18.2 antibody or antigen-binding fragment thereof of claim 1, wherein the antibody or antigen-binding fragment comprises a light chain constant domain, or the antibody or antigen-binding fragment comprises a light chain constant domain and a heavy chain constant domain.

5. A bispecific antibody, comprising a first antibody or antigen binding fragment that binds to CLDN18.2, and a second antigen binding domain that binds to CD3, wherein the first antibody or antigen binding fragment is the anti-CLDN18.2 antibody or antigen-binding fragment of claim 1.

6. The bispecific antibody of claim 5, wherein the first antibody or antigen binding fragment comprises two identical heavy chains and two identical light chains, and wherein the second antigen binding domain comprises two identical single chain antibody fragments (scFv).

7. The bispecific antibody of claim 6, wherein each of the light chains of the first antibody or antigen binding fragment thereof is fused to each of the single chain antibody fragments (scFv) of the second antigen binding domain.

8. The bispecific antibody of claim 6, wherein the single chain antibody fragment (scFv) of CD3 comprises a heavy chain variable region and a light chain variable region, wherein (1) the heavy chain variable region comprises HCDR1 comprising the amino acid sequence of SEQ ID NO. 31, HCDR2 comprising the amino acid sequence of SEQ ID NO. 32 and HCDR3 comprising the amino acid sequence of SEQ ID NO. 33, and the light chain variable region comprises LCDR1 comprising the amino acid sequence of SEQ ID NO. 34, LCDR2 comprising the amino acid sequence of SEQ ID NO. 35 and LCDR3 comprising the amino acid sequence of SEQ ID NO. 36;
(2) the heavy chain variable region comprises HCDR1 comprising the amino acid sequence of SEQ ID NO. 37, HCDR2 comprising the amino acid sequence of SEQ ID NO. 38 and HCDR3 comprising the amino acid sequence of SEQ ID NO. 39, and the light chain variable region comprises LCDR1 comprising the amino acid sequence of SEQ ID NO. 34, LCDR2 comprising the amino acid sequence of SEQ ID NO. 35 and LCDR3 comprising the amino acid sequence of SEQ ID NO. 36; or
(3) the heavy chain variable region comprises HCDR1 comprising the amino acid sequence of SEQ ID NO. 37, HCDR2 comprising the amino acid sequence of SEQ ID NO. 40 and HCDR3 comprising the amino acid sequence of SEQ ID NO. 39, and the light chain variable region comprises LCDR1 comprising the amino acid sequence of SEQ ID NO. 34, LCDR2 comprising the amino acid sequence of SEQ ID NO. 35 and LCDR3 comprising the amino acid sequence of SEQ ID NO. 36.

9. The bispecific antibody of claim 8, wherein
(1) the heavy chain variable region comprises an amino acid sequence that is at least about 95% identical to the amino acid sequence of SEQ ID NO. 25, and a light chain variable region comprises an amino acid sequence that is at least about 95% identical to the amino acid sequence of SEQ ID NO. 26;
(2) the heavy chain variable region comprises an amino acid sequence that is at least about 95% identical to the amino acid sequence of SEQ ID NO. 27, and a light chain variable region comprises an amino acid sequence that is at least about 95% identical to the amino acid sequence of SEQ ID NO. 26; or
(3) the heavy chain variable region comprises an amino acid sequence that is at least about 95% identical to the amino acid sequence of SEQ ID NO. 28, and a light chain variable region comprises an amino acid sequence that is at least about 95% identical to the amino acid sequence of SEQ ID NO. 26.

10. An isolated nucleic acid comprising a nucleic acid sequence encoding the anti-CLDN18.2 or antigen binding fragment of claim 1.

11. A vector comprising the nucleic acid of claim 10.

12. An isolated host cell comprising the anti-CLDN18.2 antibody or antigen binding fragment thereof of claim 1.

13. A pharmaceutical composition comprising the anti-CLDN18.2 antibody or antigen binding fragment of claim 1.

14. A method of treating cancer in a subject in need thereof, comprising administering to the subject the bispecific antibody of claim 8, wherein the cancer is a CLDN18.2-positive cancer.

15. The anti-CLDN18.2 antibody or antigen binding fragment thereof of claim 3, wherein
the heavy chain variable region comprises an amino acid sequence that is at least about 95% identical to the amino acid sequence of SEQ ID NO. 9, and the light chain variable region comprises an amino acid sequence that is at least about 95% identical to the amino acid sequence of SEQ ID NO. 10; or
the antibody or antigen-binding fragment thereof is a humanized antibody or antigen-binding fragment thereof, the heavy chain variable region comprises an amino acid sequence that is at least about 95% identical to the amino acid sequence of any one of SEQ ID NOs. 17-21, and the light chain variable region comprises an amino acid sequence that is at least about 95% identical to the amino acid sequence of any one of SEQ ID NOs. 22-24.

16. The bispecific antibody of claim 7, wherein the C-terminal of the constant region of each of the light chains of the first antibody or antigen binding fragment is fused to the N-terminal of the heavy chain variable region of each of the single chain antibody fragments (scFv) of the second antigen binding domain directly or via a linker.

17. A pharmaceutical composition of claim 13, wherein the pharmaceutical composition further comprises one or more pharmaceutically acceptable excipients.

18. The method of claim 14, wherein the CLDN18.2-positive cancer is hematological cancer or solid cancer.

19. The method of claim 14, wherein the CLDN18.2-positive cancer is gastric cancer or pancreatic cancer.

* * * * *

SEQUENCE LISTING

```
<160> NUMBER OF SEQ ID NOS: 52

<210> SEQ ID NO 1
<211> LENGTH: 125
<212> TYPE: PRT
<213> ORGANISM: Artificial Sequence
<220> FEATURE:
<223> OTHER INFORMATION: VH

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Asn Trp Asp Pro Tyr Tyr Tyr Tyr Tyr Gly Met
            100                 105                 110

Asp Val Trp Gly Gln Gly Thr Thr Val Thr Val Ser Ser
        115                 120                 125


<210> SEQ ID NO 2
<211> LENGTH: 107
<212> TYPE: PRT
<213> ORGANISM: Artificial Sequence
<220> FEATURE:
<223> OTHER INFORMATION: VL

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Leu
                85                  90                  95

Thr Phe Gly Gly Gly Thr Lys Val Glu Ile Lys
            100                 105


<210> SEQ ID NO 3
<211> LENGTH: 124
<212> TYPE: PRT
<213> ORGANISM: Artificial Sequence
```

-continued

<220> FEATURE:
<223> OTHER INFORMATION: VH

<400> SEQUENCE: 3

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Arg Phe Phe Asp Trp Leu Leu Gly Ser Ala Phe Asp
            100                 105                 110

Ile Trp Gly Gln Gly Thr Thr Val Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: VL

<400> SEQUENCE: 4

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105
```

<210> SEQ ID NO 5
<211> LENGTH: 118
<212> TYPE: PRT
<213> ORGANISM: Artificial Sequence
<220> FEATURE:
<223> OTHER INFORMATION: VH

<400> SEQUENCE: 5

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45
```

-continued

```
Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Ser Tyr Gly Asn Ser Phe Ala Asn Trp Gly Gln Gly Thr
            100                 105                 110

Leu Val Thr Val Ser Ser
        115
```

<210> SEQ ID NO 6
<211> LENGTH: 113
<212> TYPE: PRT
<213> ORGANISM: Artificial Sequence
<220> FEATURE:
<223> OTHER INFORMATION: VL

<400> SEQUENCE: 6

```
Asp Ile Gln Ile Thr Gln Ser Pro Ser Ser Leu Thr Val Thr Ala Gly
1               5                   10                  15

Glu Lys Val Thr Met Ser Cys Gln Ser Ser Gln Ser Leu Leu Asn Ser
            20                  25                  30

Gly Asn His Arg Asn Tyr Leu Thr Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ala Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Thr Tyr Tyr Tyr Pro Phe Thr Phe Gly Ser Gly Thr Lys Leu Glu Ile
            100                 105                 110

Lys
```

<210> SEQ ID NO 7
<211> LENGTH: 119
<212> TYPE: PRT
<213> ORGANISM: Artificial Sequence
<220> FEATURE:
<223> OTHER INFORMATION: VH

<400> SEQUENCE: 7

```
Asp Val Gln Leu Gln Gln Ser Gly Pro Glu Leu Met Lys Pro Gly Ala
1               5                   10                  15

Ser Val Lys Ile Ser Cys Lys Ala Ser Asp Tyr Ser Phe Thr Ser Tyr
            20                  25                  30

Asn Met His Trp Val Lys Gln Ser His Gly Lys Ser Leu Glu Trp Ile
        35                  40                  45

Gly Tyr Ile Asp Pro Phe Asn Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Ile Ser Ser Leu Thr Ser Glu Asp Ser Ala Val Tyr Tyr Cys
                85                  90                  95

Ala Arg Gly Ala Tyr Tyr Gly Asn Ser Phe Asp Tyr Trp Gly Gln Gly
            100                 105                 110
```

```
Thr Leu Val Thr Val Ser Ser
        115


<210> SEQ ID NO 8
<211> LENGTH: 113
<212> TYPE: PRT
<213> ORGANISM: Artificial Sequence
<220> FEATURE:
<223> OTHER INFORMATION: VL

<400> SEQUENCE: 8

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Asn Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Gly Ser Val Gln Ala Glu Asp Leu Ala Val Tyr Tyr Cys Gln Asn
                85                  90                  95

Ala Tyr Ser Phe Pro Phe Thr Phe Gly Ser Gly Thr Lys Leu Glu Ile
            100                 105                 110

Lys


<210> SEQ ID NO 9
<211> LENGTH: 118
<212> TYPE: PRT
<213> ORGANISM: Artificial Sequence
<220> FEATURE:
<223> OTHER INFORMATION: VH

<400> SEQUENCE: 9

Gln Leu Gln Leu Gln Gln Ser Gly Thr Glu Leu Val Arg Pro Gly Ser
1               5                   10                  15

Ser Val Lys Ile Ser Cys Lys Ala Ser Gly Tyr Ala Phe Ser Asn Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asn Gly Asp Thr Lys Tyr Asn Gly Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Phe Cys
                85                  90                  95

Ala Arg Tyr Tyr Arg Gly Asn Cys Phe Asp Tyr Trp Gly Gln Gly Thr
            100                 105                 110

Thr Leu Thr Val Ser Ser
        115


<210> SEQ ID NO 10
<211> LENGTH: 113
<212> TYPE: PRT
<213> ORGANISM: Artificial Sequence
<220> FEATURE:
<223> OTHER INFORMATION: VL

<400> SEQUENCE: 10
```

```
Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Ala Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Asn
                85                  90                  95

Ala Tyr Thr Tyr Pro Leu Thr Phe Gly Ala Gly Thr Lys Leu Glu Ile
            100                 105                 110

Lys


<210> SEQ ID NO 11
<211> LENGTH: 10
<212> TYPE: PRT
<213> ORGANISM: Artificial Sequence
<220> FEATURE:
<223> OTHER INFORMATION: CDR1

<400> SEQUENCE: 11

Gly Tyr Ala Phe Ser Asn Tyr Trp Met Asn
1               5                   10


<210> SEQ ID NO 12
<211> LENGTH: 17
<212> TYPE: PRT
<213> ORGANISM: Artificial Sequence
<220> FEATURE:
<223> OTHER INFORMATION: CDR2

<400> SEQUENCE: 12

Gln Ile Tyr Pro Gly Asn Gly Asp Thr Lys Tyr Asn Gly Asn Phe Lys
1               5                   10                  15

Gly


<210> SEQ ID NO 13
<211> LENGTH: 9
<212> TYPE: PRT
<213> ORGANISM: Artificial Sequence
<220> FEATURE:
<223> OTHER INFORMATION: CDR3

<400> SEQUENCE: 13

Tyr Tyr Arg Gly Asn Cys Phe Asp Tyr
1               5


<210> SEQ ID NO 14
<211> LENGTH: 17
<212> TYPE: PRT
<213> ORGANISM: Artificial Sequence
<220> FEATURE:
<223> OTHER INFORMATION: CDR1

<400> SEQUENCE: 14

Lys Ser Ser Gln Ser Leu Leu Asn Ser Gly Asn Gln Lys Asn Tyr Leu
1               5                   10                  15

Thr
```

<210> SEQ ID NO 15
<211> LENGTH: 7
<212> TYPE: PRT
<213> ORGANISM: Artificial Sequence
<220> FEATURE:
<223> OTHER INFORMATION: CDR2

<400> SEQUENCE: 15

```
Trp Ala Ser Thr Arg Asp Ser
1               5
```

<210> SEQ ID NO 16
<211> LENGTH: 9
<212> TYPE: PRT
<213> ORGANISM: Artificial Sequence
<220> FEATURE:
<223> OTHER INFORMATION: CDR3

<400> SEQUENCE: 16

```
Gln Asn Ala Tyr Thr Tyr Pro Leu Thr
1               5
```

<210> SEQ ID NO 17
<211> LENGTH: 118
<212> TYPE: PRT
<213> ORGANISM: Artificial Sequence
<220> FEATURE:
<223> OTHER INFORMATION: VH1

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Tyr
            20                  25                  30

Trp Met Asn Trp Val Arg Gln Ala Pro Gly Gln Arg Leu Glu Trp Met
        35                  40                  45

Gly Gln Ile Tyr Pro Gly Asn Gly Asp Thr Lys Tyr Asn Gly Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Arg Gly Asn Cys Phe Asp Tyr Trp Gly Gln Gly Thr
            100                 105                 110

Leu Val Thr Val Ser Ser
        115
```

<210> SEQ ID NO 18
<211> LENGTH: 118
<212> TYPE: PRT
<213> ORGANISM: Artificial Sequence
<220> FEATURE:
<223> OTHER INFORMATION: VH2

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Tyr
            20                  25                  30

Trp Met Asn Trp Val Arg Gln Ala Pro Gly Gln Gly Leu Glu Trp Ile
        35                  40                  45
```

-continued

```
Gly Gln Ile Tyr Pro Gly Asn Gly Asp Thr Lys Tyr Asn Gly Asn Phe
    50                  55                  60

Lys Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Tyr Arg Gly Asn Cys Phe Asp Tyr Trp Gly Gln Gly Thr
            100                 105                 110

Leu Val Thr Val Ser Ser
        115


<210> SEQ ID NO 19
<211> LENGTH: 118
<212> TYPE: PRT
<213> ORGANISM: Artificial Sequence
<220> FEATURE:
<223> OTHER INFORMATION: VH3

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Tyr
            20                  25                  30

Trp Met Asn Trp Val Lys Gln Ala Pro Gly Gln Gly Leu Glu Trp Ile
        35                  40                  45

Gly Gln Ile Tyr Pro Gly Asn Gly Asp Thr Lys Tyr Asn Gly Asn Phe
    50                  55                  60

Lys Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Tyr Arg Gly Asn Cys Phe Asp Tyr Trp Gly Gln Gly Thr
            100                 105                 110

Leu Val Thr Val Ser Ser
        115


<210> SEQ ID NO 20
<211> LENGTH: 118
<212> TYPE: PRT
<213> ORGANISM: Artificial Sequence
<220> FEATURE:
<223> OTHER INFORMATION: VH4

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Tyr
            20                  25                  30

Trp Met Asn Trp Val Lys Gln Ala Pro Gly Gln Gly Leu Glu Trp Ile
        35                  40                  45

Gly Gln Ile Tyr Pro Gly Asn Gly Asp Thr Lys Tyr Asn Gly Asn Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Tyr Arg Gly Asn Cys Phe Asp Tyr Trp Gly Gln Gly Thr
```

```
            100                 105                 110

Leu Val Thr Val Ser Ser
        115


<210> SEQ ID NO 21
<211> LENGTH: 118
<212> TYPE: PRT
<213> ORGANISM: Artificial Sequence
<220> FEATURE:
<223> OTHER INFORMATION: VH5

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Tyr
            20                  25                  30

Trp Met Asn Trp Val Lys Gln Ala Pro Gly Gln Gly Leu Glu Trp Ile
        35                  40                  45

Gly Gln Ile Tyr Pro Gly Asn Gly Asp Thr Lys Tyr Asn Gly Asn Phe
    50                  55                  60

Lys Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Tyr Arg Gly Asn Cys Phe Asp Tyr Trp Gly Gln Gly Thr
            100                 105                 110

Leu Val Thr Val Ser Ser
        115


<210> SEQ ID NO 22
<211> LENGTH: 113
<212> TYPE: PRT
<213> ORGANISM: Artificial Sequence
<220> FEATURE:
<223> OTHER INFORMATION: VL1

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Leu Thr Phe Gly Gly Gly Thr Lys Val Glu Ile
            100                 105                 110

Lys


<210> SEQ ID NO 23
<211> LENGTH: 113
<212> TYPE: PRT
<213> ORGANISM: Artificial Sequence
<220> FEATURE:
<223> OTHER INFORMATION: VL2
```

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Ala Tyr Thr Tyr Pro Leu Thr Phe Gly Gly Gly Thr Lys Val Glu Ile
            100                 105                 110

Lys

<210> SEQ ID NO 24
<211> LENGTH: 113
<212> TYPE: PRT
<213> ORGANISM: Artificial Sequence
<220> FEATURE:
<223> OTHER INFORMATION: VL3

<400> SEQUENCE: 24

Asp Ile Val Met Thr Gln Ser Pro Asp Ser Leu Ala Val Ser Leu Gly
1               5                   10                  15

Glu Arg Ala Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Ala Tyr Thr Tyr Pro Leu Thr Phe Gly Gly Gly Thr Lys Val Glu Ile
            100                 105                 110

Lys

<210> SEQ ID NO 25
<211> LENGTH: 125
<212> TYPE: PRT
<213> ORGANISM: Artificial Sequence
<220> FEATURE:
<223> OTHER INFORMATION: VH

<400> SEQUENCE: 25

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp

```
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125


<210> SEQ ID NO 26
<211> LENGTH: 109
<212> TYPE: PRT
<213> ORGANISM: Artificial Sequence
<220> FEATURE:
<223> OTHER INFORMATION: VL

<400> SEQUENCE: 26

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105


<210> SEQ ID NO 27
<211> LENGTH: 125
<212> TYPE: PRT
<213> ORGANISM: Artificial Sequence
<220> FEATURE:
<223> OTHER INFORMATION: VH

<400> SEQUENCE: 27

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Arg Thr Glu Asp Thr Ala Val Tyr
                85                  90                  95

Tyr Cys Val Arg His Gly Asn Trp Gly Asn Ser Tyr Ile Ser Tyr Trp
            100                 105                 110

Ala Tyr Trp Gly Gln Gly Thr Thr Val Thr Val Ser Ser
        115                 120                 125
```

-continued

<210> SEQ ID NO 28
<211> LENGTH: 125
<212> TYPE: PRT
<213> ORGANISM: Artificial Sequence
<220> FEATURE:
<223> OTHER INFORMATION: VH

<400> SEQUENCE: 28

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Thr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Arg Thr Glu Asp Thr Ala Val Tyr
                85                  90                  95

Tyr Cys Val Arg His Gly Asn Trp Gly Asn Ser Tyr Ile Ser Tyr Trp
            100                 105                 110

Ala Tyr Trp Gly Gln Gly Thr Thr Val Thr Val Ser Ser
        115                 120                 125

<210> SEQ ID NO 29
<211> LENGTH: 118
<212> TYPE: PRT
<213> ORGANISM: Artificial Sequence
<220> FEATURE:
<223> OTHER INFORMATION: VH

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ser Tyr Gly Asn Ser Phe Ala Asn Trp Gly Gln Gly Thr
            100                 105                 110

Thr Val Thr Val Ser Ser
        115

<210> SEQ ID NO 30
<211> LENGTH: 113
<212> TYPE: PRT
<213> ORGANISM: Artificial Sequence
<220> FEATURE:
<223> OTHER INFORMATION: VL

<400> SEQUENCE: 30

Asp Ile Val Ile Thr Gln Ser Pro Ser Ser Leu Ser Val Thr Leu Gly

-continued

```
1               5                   10                  15

Glu Arg Ala Thr Leu Ser Cys Arg Ser Ser Gln Ser Leu Leu Asn Ser
            20                  25                  30

Gly Asn His Arg Asn Tyr Leu Thr Trp Tyr Gln Gln Lys Pro Gly Gln
        35                  40                  45

Ala Pro Arg Leu Leu Met Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Asn
                85                  90                  95

Thr Tyr Tyr Tyr Pro Phe Thr Phe Gly Gly Gly Thr Lys Leu Glu Ile
            100                 105                 110

Lys


<210> SEQ ID NO 31
<211> LENGTH: 5
<212> TYPE: PRT
<213> ORGANISM: Artificial Sequence
<220> FEATURE:
<223> OTHER INFORMATION: CDR1

<400> SEQUENCE: 31

Lys Tyr Ala Met Asn
1               5


<210> SEQ ID NO 32
<211> LENGTH: 19
<212> TYPE: PRT
<213> ORGANISM: Artificial Sequence
<220> FEATURE:
<223> OTHER INFORMATION: CDR2

<400> SEQUENCE: 32

Arg Ile Arg Ser Lys Tyr Asn Asn Tyr Ala Thr Tyr Tyr Ala Asp Ser
1               5                   10                  15

Val Lys Asp


<210> SEQ ID NO 33
<211> LENGTH: 14
<212> TYPE: PRT
<213> ORGANISM: Artificial Sequence
<220> FEATURE:
<223> OTHER INFORMATION: CDR3

<400> SEQUENCE: 33

His Gly Asn Phe Gly Asn Ser Tyr Ile Ser Tyr Trp Ala Tyr
1               5                   10


<210> SEQ ID NO 34
<211> LENGTH: 14
<212> TYPE: PRT
<213> ORGANISM: Artificial Sequence
<220> FEATURE:
<223> OTHER INFORMATION: CDR1

<400> SEQUENCE: 34

Gly Ser Ser Thr Gly Ala Val Thr Ser Gly Tyr Tyr Pro Asn
1               5                   10


<210> SEQ ID NO 35
<211> LENGTH: 7
```

<212> TYPE: PRT
<213> ORGANISM: Artificial Sequence
<220> FEATURE:
<223> OTHER INFORMATION: CDR2

<400> SEQUENCE: 35

Gly Thr Lys Phe Leu Ala Pro
1               5

<210> SEQ ID NO 36
<211> LENGTH: 9
<212> TYPE: PRT
<213> ORGANISM: Artificial Sequence
<220> FEATURE:
<223> OTHER INFORMATION: CDR3

<400> SEQUENCE: 36

Ala Leu Trp Tyr Ser Asn Arg Trp Val
1               5

<210> SEQ ID NO 37
<211> LENGTH: 5
<212> TYPE: PRT
<213> ORGANISM: Artificial Sequence
<220> FEATURE:
<223> OTHER INFORMATION: CDR1

<400> SEQUENCE: 37

Thr Tyr Ala Met Asn
1               5

<210> SEQ ID NO 38
<211> LENGTH: 19
<212> TYPE: PRT
<213> ORGANISM: Artificial Sequence
<220> FEATURE:
<223> OTHER INFORMATION: CDR2

<400> SEQUENCE: 38

Arg Ile Arg Ser Lys Tyr Asn Asn Tyr Ala Thr Tyr Tyr Ala Asp Ser
1               5                   10                  15

Val Lys Asp

<210> SEQ ID NO 39
<211> LENGTH: 14
<212> TYPE: PRT
<213> ORGANISM: Artificial Sequence
<220> FEATURE:
<223> OTHER INFORMATION: CDR3

<400> SEQUENCE: 39

His Gly Asn Trp Gly Asn Ser Tyr Ile Ser Tyr Trp Ala Tyr
1               5                   10

<210> SEQ ID NO 40
<211> LENGTH: 19
<212> TYPE: PRT
<213> ORGANISM: Artificial Sequence
<220> FEATURE:
<223> OTHER INFORMATION: CDR2

<400> SEQUENCE: 40

Arg Ile Arg Ser Lys Tyr Asn Asn Tyr Ala Thr Thr Tyr Ala Asp Ser
1               5                   10                  15

Val Lys Asp

<210> SEQ ID NO 41
<211> LENGTH: 15
<212> TYPE: PRT
<213> ORGANISM: Artificial Sequence
<220> FEATURE:
<223> OTHER INFORMATION: Linker-1

<400> SEQUENCE: 41

```
Gly Gly Gly Gly Ser Gly Gly Gly Gly Ser Gly Gly Gly Gly Ser
1               5                   10                  15
```

<210> SEQ ID NO 42
<211> LENGTH: 30
<212> TYPE: PRT
<213> ORGANISM: Artificial Sequence
<220> FEATURE:
<223> OTHER INFORMATION: Linker-2

<400> SEQUENCE: 42

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 43
<211> LENGTH: 109
<212> TYPE: PRT
<213> ORGANISM: Artificial Sequence
<220> FEATURE:
<223> OTHER INFORMATION: CL (constant region of human kappa light chain)

<400> SEQUENCE: 43

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Thr Ser
            100                 105
```

<210> SEQ ID NO 44
<211> LENGTH: 98
<212> TYPE: PRT
<213> ORGANISM: Artificial Sequence
<220> FEATURE:
<223> OTHER INFORMATION: CH1 of human IgG1 heavy chain

<400> SEQUENCE: 44

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 45
<211> LENGTH: 15
<212> TYPE: PRT
<213> ORGANISM: Artificial Sequence
<220> FEATURE:
<223> OTHER INFORMATION: Hinge

<400> SEQUENCE: 45

Glu Pro Lys Ser Cys Asp Lys Thr His Thr Cys Pro Pro Cys Pro
1               5                   10                  15


<210> SEQ ID NO 46
<211> LENGTH: 110
<212> TYPE: PRT
<213> ORGANISM: Artificial Sequence
<220> FEATURE:
<223> OTHER INFORMATION: CH2 of human IgGl heavy chain

<400> SEQUENCE: 46

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Ala Ala Pro Ile Glu Lys Thr Ile Ser Lys Ala Lys
            100                 105                 110


<210> SEQ ID NO 47
<211> LENGTH: 107
<212> TYPE: PRT
<213> ORGANISM: Artificial Sequence
<220> FEATURE:
<223> OTHER INFORMATION: CH3 of human IgGl heavy chain

<400> SEQUENCE: 47

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80
```

-continued

```
Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 48
<211> LENGTH: 330
<212> TYPE: PRT
<213> ORGANISM: Artificial Sequence
<220> FEATURE:
<223> OTHER INFORMATION: constant region of mouse IgG2a heavy chain

<400> SEQUENCE: 48

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

-continued

<210> SEQ ID NO 49
<211> LENGTH: 16
<212> TYPE: PRT
<213> ORGANISM: Artificial Sequence
<220> FEATURE:
<223> OTHER INFORMATION: hinge area of constant region of mouse IgG2a heavy chain

<400> SEQUENCE: 49

```
Glu Pro Arg Gly Pro Thr Ile Lys Pro Cys Pro Pro Cys Lys Cys Pro
1               5                   10                  15
```

<210> SEQ ID NO 50
<211> LENGTH: 97
<212> TYPE: PRT
<213> ORGANISM: Artificial Sequence
<220> FEATURE:
<223> OTHER INFORMATION: CH1 of constant region of mouse IgG2a heavy chain

<400> SEQUENCE: 50

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile
```

<210> SEQ ID NO 51
<211> LENGTH: 217
<212> TYPE: PRT
<213> ORGANISM: Artificial Sequence
<220> FEATURE:
<223> OTHER INFORMATION: CH2+CH3 of constant region of mouse IgG2a heavy chain

<400> SEQUENCE: 51

```
Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys Gly Ser
            100                 105                 110

Val Arg Ala Pro Gln Val Tyr Val Leu Pro Pro Pro Glu Glu Glu Met
```

-continued

```
        115                 120                 125

Thr Lys Lys Gln Val Thr Leu Thr Cys Met Val Thr Asp Phe Met Pro
    130                 135                 140

Glu Asp Ile Tyr Val Glu Trp Thr Asn Asn Gly Lys Thr Glu Leu Asn
145                 150                 155                 160

Tyr Lys Asn Thr Glu Pro Val Leu Asp Ser Asp Gly Ser Tyr Phe Met
                165                 170                 175

Tyr Ser Lys Leu Arg Val Glu Lys Lys Asn Trp Val Glu Arg Asn Ser
            180                 185                 190

Tyr Ser Cys Ser Val Val His Glu Gly Leu His Asn His His Thr Thr
        195                 200                 205

Lys Ser Phe Ser Arg Thr Pro Gly Lys
    210                 215


<210> SEQ ID NO 52
<211> LENGTH: 107
<212> TYPE: PRT
<213> ORGANISM: Artificial Sequence
<220> FEATURE:
<223> OTHER INFORMATION: CL (constant region of mouse kappa light chain)

<400> SEQUENCE: 52

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```